(12) United States Patent
O'Connor

(10) Patent No.: US 7,829,535 B2
(45) Date of Patent: *Nov. 9, 2010

(54) METHODS FOR BONE TREATMENT BY MODULATING AN ARACHIDONIC ACID METABOLIC OR SIGNALING PATHWAY

(75) Inventor: James Patrick O'Connor, Menlo Park, CA (US)

(73) Assignee: Accelalox, Inc., Menlo Park, CA (US)

( * ) Notice: Subject to any disclaimer, the term of this patent is extended or adjusted under 35 U.S.C. 154(b) by 324 days.

This patent is subject to a terminal disclaimer.

(21) Appl. No.: 11/995,529

(22) PCT Filed: Aug. 18, 2006

(86) PCT No.: PCT/US2006/032367
§ 371 (c)(1),
(2), (4) Date: Jul. 14, 2008

(87) PCT Pub. No.: WO2007/022427
PCT Pub. Date: Feb. 22, 2007

(65) Prior Publication Data
US 2008/0280826 A1 Nov. 13, 2008

Related U.S. Application Data

(60) Provisional application No. 60/709,838, filed on Aug. 18, 2005.

(51) Int. Cl.
*A61K 38/00* (2006.01)
*A61K 31/70* (2006.01)
*A61K 31/445* (2006.01)
*A61K 31/40* (2006.01)
*A61K 31/195* (2006.01)
*A61K 47/00* (2006.01)

(52) U.S. Cl. ............... 514/12; 514/44; 514/321; 514/409; 514/567; 514/772

(58) Field of Classification Search ............ 514/12, 514/44, 321, 409, 567, 772
See application file for complete search history.

(56) References Cited

U.S. PATENT DOCUMENTS

| 7,291,638 | B2 | 2/2007 | O'Connor |
| 2003/0175680 | A1 | 9/2003 | Allard et al. |
| 2004/0138262 | A1 | 7/2004 | Chantigny et al. |
| 2005/0032747 | A1 | 2/2005 | Bartolini et al. |
| 2005/0058734 | A1 | 3/2005 | Burch et al. |
| 2008/0033033 | A1 | 2/2008 | Kambe et al. |

FOREIGN PATENT DOCUMENTS

| WO | WO 01/41753 A2 | 6/2001 |
| WO | WO 03/020267 A1 | 3/2003 |
| WO | WO 2005/123130 A2 | 12/2005 |

OTHER PUBLICATIONS

PCT International Search Report and Written Opinion, PCT/US2006/032367, Jul. 10, 2007, 11 pages.
PCT International Preliminary Report on Patentability, PCT/US2006/032367, Jan. 7, 2008, 12 pages.
Office Action for Israel Patent Application No. 18955, Apr. 21, 2010, 4 pages.
PCT International Search Report and Written Opinion, PCT/US2009/034790, Jul. 23, 2009, 15 pages.
Examination Report, New Zealand Patent Application No. 566283, Feb. 24, 2010, 2 pages.
Supplementary European Search Report, European Patent Application No. EP 06801878, Mar. 17, 2010, 12 pages.
Response to European Search Report and Exhibits A-F, European Patent Application No. EP 06801878, Jun. 16, 2010, 12 pages.
Exhibit E—Abstract for two articles by J.L. Collins (1. Collins, J.W., et al., "The Role of Leukotrienes in Force-induced Bone Development," Department of Orthodontics, CWRU School of Dentistry, J. Dent. Res., 1987, vol. 66, No. 1722; and 2. Collins, J.W., et al., "Stimulation of Bone Development by Mechanical Stress and Inhibition of Leukotriene Biosynthesis," Department of Orthodontics, CWRU School of Dentistry, Program of the 65th General Session, International Association for Dental Research Annual Session, American Association for Dental Research, Chicago, 1987, p. 328.), Cariology/Craniofacial, p. 28, filed with European Patent Office for European Patent Application No. 06801878.7 on Jun. 16, 2010.
Exhibit D—List of abstracts of relevant review articles published in 2003-2005, filed with European Patent Office for European Patent Application No. 06801878.7 on Jun. 16, 2010, 5 pages.
Exhibit F—Product data sheet, Enzo Life Sciences, can be retrieved at <URL:http://www.enzolifesciences.com/fileadmin/enzo/BML/ei101.PDF>, and filed with European Patent Office for European Patent Application No. 06801878.7 on Jun. 16, 2010, 1 page.
Bonewald, L., et al., "Mice Lacking 5-Lipoxygenase Have Increased Cortical Bone Thickness," Advances in Experimental Medicine and Biology, 1997, pp. 299-302, vol. 433, 1997.
Burd, T. A., M. S. Hughes, et al. (2003). "Heterotopic ossification prophylaxis with indomethacin increases the risk of long-bone nonunion." J Bone Joint Surg Br 85-B(5): 700-705.

(Continued)

*Primary Examiner*—Raymond J Henley, III
(74) *Attorney, Agent, or Firm*—Fenwick & West LLP

(57) ABSTRACT

Methods for promoting osteogenesis to accelerate or enhance bone fracture healing, treat bone defects, and enhance bone formation are disclosed. The methods modulate an arachidonic acid metabolic or signaling pathway in general, and, in particular, utilize 5-lipoxygenase inhibitors. These molecules can be delivered alone or in combination with one or more agents that inhibit bone resorption, regulate calcium resorption from bone, enhance bone accumulation, enhance bone formation, induce bone formation, impair growth of microorganisms, reduce inflammation, and/or reduce pain.

25 Claims, 8 Drawing Sheets

OTHER PUBLICATIONS

Burd, T. A., K. J. Lowry, et al. (2001). "Indomethacin Compared with Localized Irradiation for the Prevention of Heterotopic Ossification Following Surgical Treatment of Acetabular Fractures." J Bone Joint Surg Am 83(12): 1783-1788.

Collins, J.W., et al., "The Role of Leukotrienes in Force-induced Bone Development," J. Dent. Res., 1987, p. 328, vol. 66, No. 1772. (Abstract).

Collins, J.W., et al., "Stimulation of Bone Development by Mechanical Stress and Inhibition of Leukotriene Biosynthesis," J. Dent. Res., 1987, p. 328, vol. 66, No. 1771. (Abstract).

Cottrell, J., O'Connor, J.P., "Effect of Non-Steroidal Anti-Inflammatory Drugs on Bone Healing," Pharmaceuticals, 2010, vol. 3, pp. 1668-1693.

Erdmann, L., et al., "Degradable poly(anhydride ester) implants: effects of localized salicylic acid release on bone," Biomaterials, 2000, pp. 2507-2512, vol. 21.

Fijn, R., Koorevaar, R. Th. (2003). "Prevention of heterotopic ossification after total hip replacement with NSAIDs." Parmacy World & Science 25(4): 138-145.

Gerstenfeld, L.C., et al., "Impaired Fracture Healing in the Absence of TNF-] Signaling: The Role of TNF-α in Endochondral Cartilage Resorption," Journal of Bone and Mineral Research, 2003, pp. 1584-1592, vol. 18, No. 9.

Gallwitz, W., et al., "5-Lipoxygenase Metabolites of Arachidonic Acid Stimulate Isolated Osteoclasts to Resorb Calcified Matrices," The Journal of Biological Chemistry, May 15, 1993, pp. 10087-10094, vol. 268, No. 14.

Harten, R., et al., "Salicylic acid-derived poly(anhydride-esters) inhibit bone resorption and formation in vivo," J. Biomed. Mat. Res., 2005, pp. 354-362, vol. 72A No. 4.

Hungin, A.P.S., et al., "Nonsteroidal Anti-Inflammatory Drugs: Overused or Underused in Osteoarthritis?," The American Journal of Medicine, Jan. 8, 2001, pp. 8S-11S, vol. 110(1A).

Koivukangas, A., et al., "Long-Term Administration of Clodronate Does Not Prevent Fracture Healing in Rats," Clinical Orthopaedics and Related Research, 2003, pp. 268-278, No. 408.

Knelles, D., T. Barthel, et al. (1997). "Prevention of Heterotopic Ossification After Total Hip Replacement: A Prospective, Randomised Study Using Acetysalicyclic Acid, Indomethacin and Fractional or Single-Dose Irradiation." J Bone Joint Surg Br 79-B(4): 596-602.

Moed, B. R. and D. E. Karges (1994). "Prophylactic Indomethacin for the Prevention of Heterotopic Ossification After Acetabular Fracture Surgery in High-Risk Patients." Journal of Orthopaedic Trauma 8(1): 34-39.

O'Connor, J.P., et al., "Accelerating Fracture Healing by Manipulating Arachidonic Acid Metabolism," Orthopaedics, Journal of Bone and Mineral Research, Sep. 2005, p. S353, vol. 20, No. 9, Suppl. 1.

Ren, W., et al., "Effects of Leukotrienes on Osteoblastic Cell Proliferation," Calcified Tissue International, 1991, pp. 197-201, vol. 49.

Moed, B. R. and J. W. Maxey (1993). "The Effect of Indomethacin on Heterotopic Ossification Following Acetabular Fracture Surgery." Journal of Orthopaedic Trauma 7(1): 33-38.

Ritter, M. A. and J. M. Sieber (1985). "Prophylactic Indomethacin for the Prevention of Heterotopic Bone Formation Following Total Hip Arthroplasty." Clinical Orthopaedics and Related Research 196: 217-225.

Rodan, G., et al., "Osteoporosis And Bisphosphonates," The Journal of Bone & Joint Surgery, 2003, pp. 8-12, vol. 85-A, Supp. 3.

Rozental, T., et al., "Comparison of Radiographic Fracture Healing in the Distal Radius for Patients on and off Bisphosphonate Therapy," JHS, Apr. 2009, pp. 595-602, vol. 34A.

Sodemann, B., P.-E. Persson, et al. (1988). "Prevention of Heterotopic Ossification by Nonsteroid Antiinflammatory Drugs After Total Hip Arthroplasty." Clinical Orthopaedics and Related Research 237: 158-163.

Traianedes, K., et al., "5-Lipxygenase Metabolites Inhibit Bone Formation in Vitro," Endocrinology Jul. 1998, pp. 3178-3184, vol. 139, No. 7.

Vielpeau, C., J.-M. Joubert, et al. (1999). "Naproxen in the Prevention of Heterotopic Ossification After Total Hip Replacement." Clinical Orthopaedics and Related Research 369: 279-288.

FIG. 6A Cox1-/-
FIG. 6D Cox2-/-
FIG. 6B Cox1-/- (5X)
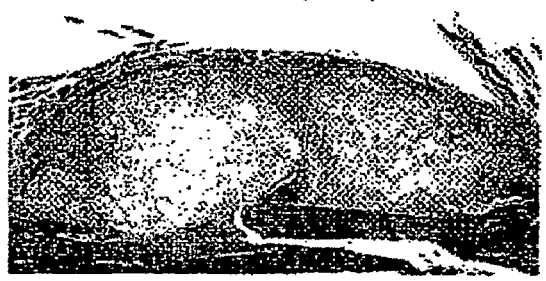
FIG. 6E Cox2-/- (10X)
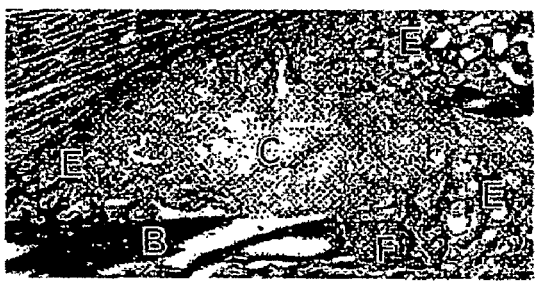
FIG. 6C Cox1-/- (10X)
FIG. 6F Cox2-/- (25X)

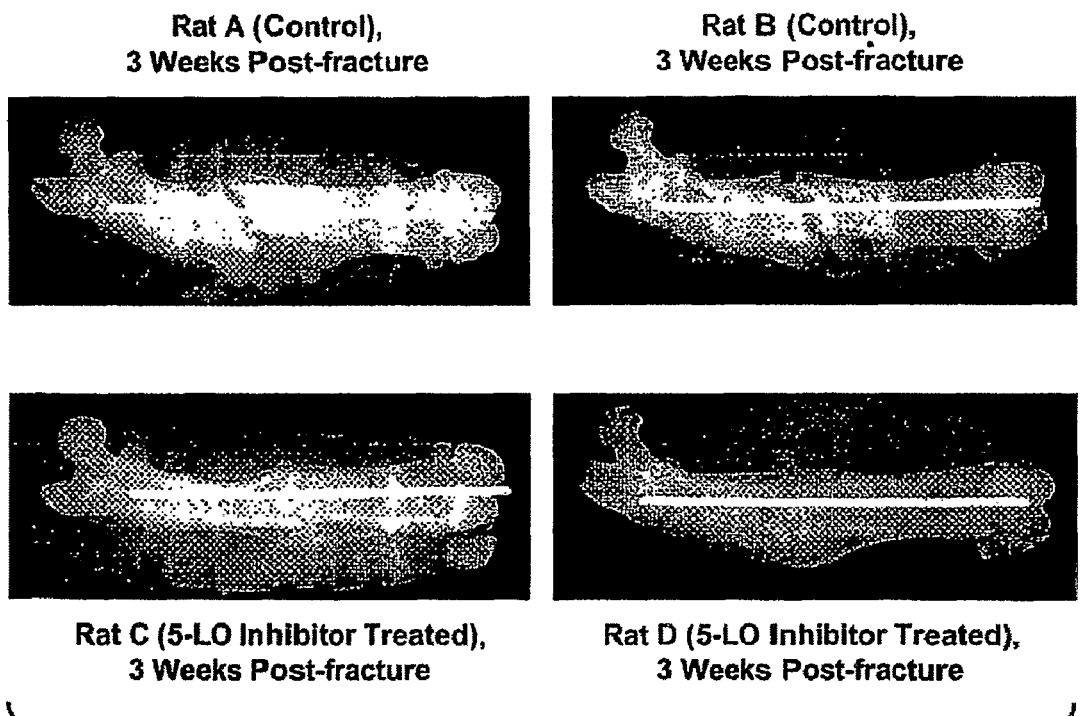
FIG. 7
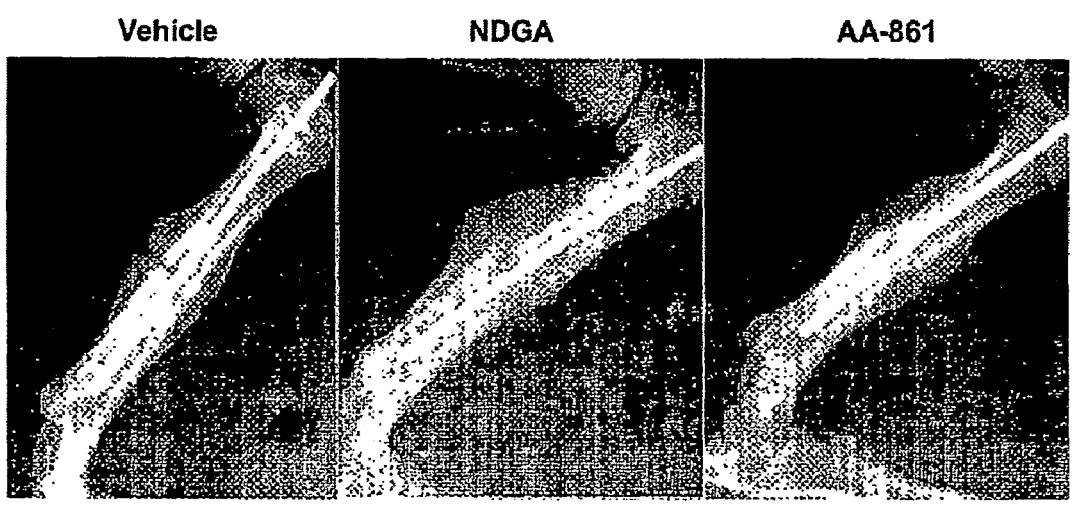
FIG. 8A  FIG. 8B  FIG. 8C

METHODS FOR BONE TREATMENT BY MODULATING AN ARACHIDONIC ACID METABOLIC OR SIGNALING PATHWAY

CROSS REFERENCE TO RELATED APPLICATIONS

This application is the National Stage of International Application No. PCT/US2006/032367, published in English under PCT Article 21(2), filed Aug. 18, 2006, which claims the benefit of U.S. Provisional Application Ser. No. 60/709,838, filed on Aug. 18, 2005, both of which are incorporated by reference in their entirety.

FIELD OF INVENTION

The invention relates generally to accelerating or enhancing bone formation or fracture healing by modulating an arachidonic acid metabolic or signaling pathway, in particular by using inhibitors of 5-lipoxygenase activity.

BACKGROUND OF THE INVENTION

Bone fractures are a common traumatic injury. Approximately 8-10 million bone fractures are reported annually in the United States with more than 1 million of these requiring hospitalization. The estimated annual costs of treating these fractures exceeds 20 billion dollars. While this is already significant, these numbers are expected to increase due to the aging of the general population. Further, among military personnel, bone fractures are common training injuries. Bone fractures, typically located in the arms and legs, are also common battle wounds. Aside from traumatic injury, bone fractures also can be caused by disease. Osteoporosis is caused by a reduction in bone mineral density in mature bone and results in fractures after minimal trauma. The disease is widespread and has a tremendous economic impact. The most common fractures occur in the vertebrae, distal radius and hip. An estimated one-third of the female population over age 65 will have vertebral fractures, caused in part by osteoporosis. Moreover, hip fractures are likely to occur in about one in every three woman and one in every six men by extreme old age.

Fracture healing is a complex tissue regeneration process that involves cell migration, proliferation, apoptosis, and differentiation in response to growth factors, cytokines, other signaling molecules, and to the mechanical environment. The temporal order and magnitude of each cellular process must be controlled for optimal regeneration. The normal events of fracture healing are described below as occurring in 4 phases. In the initial phase, hematoma formation and localized tissue hypoxia are the initial cellular and molecular events of fracture healing. The second phase, called the early stage, is characterized by inflammation followed by rapid accumulation of cells at the fracture site. The presence of macrophages and neutrophils at the fracture site during inflammation precedes the rapid migration and proliferation of mesenchymal cells at the fracture site. In the third, regenerative phase, endochondral ossification creates the new bone which bridges the fracture. At this point, the fracture callus has a well-defined morphology. Intramembraneous ossification creates buttresses of periosteal bone at the callus periphery. Mesenchymal cells within the callus begin to differentiate into chondrocytes at the interface of the periosteal bone buttress. Each new chondrocyte develops as would be expected with matrix deposition followed by matrix calcification to produce calcified cartilage and then apoptosis. Channels are formed into the calcified cartilage starting at the periosteal bone buttresses. Osteoblasts migrate or differentiate on the surface of the calcified cartilage within these channels and begin depositing new bone. As chondrocyte differentiation proceeds from the periphery to the center of the callus (fracture site), channel formation, osteoblast differentiation, and new bone formation follows until the soft callus has been replaced with woven (immature) bone. Angiogenesis during the regenerative phase is essential. The immature woven bone created during the regenerative phase is mechanically unsuited for normal weight-bearing. To compensate for the decreased mechanical properties of the woven bone, the fracture callus has a significantly larger diameter which provides for greater structural mechanical properties. In the final, remodeling phase, fracture callus diameter diminishes until the bone obtains its normal dimensions while maintaining the bones overall mechanical properties by enhancing material mechanical properties. This is accomplished by replacing the mechanically poor, woven bone with mechanically strong, lamellar (mature) bone. In successive rounds, osteoclasts resorb the woven bone and osteoblasts replace it with lamellar bone. Molecular mechanisms governing osteoclast formation and function occurs through the RANKL-RANK pathway and this pathway is activated during fracture healing.

Fractures are generally treated conservatively by closed reduction of the fracture and immobilization (casting) of the affected bone. In such cases, the bone heals through the endochondral ossification pathway described above. Adequate nutrition to include vitamin C, vitamin D, and calcium aids in healing. There has been no major advancement in the treatment of bone fractures since the mid $20^{th}$ century when open reduction and internal fixation of fractures became commonplace. The promise of growth factor treatments to enhance fracture healing has not been realized yet.

Unfortunately, many fractures require surgical intervention to increase healing success and reduce the likelihood of complication. There is only one approved pharmacological enhancement for bone healing and that is treatment with recombinant bone morphogenetic protein, either BMP-2 or BMP-7 (OP-1). Use of these growth factors requires surgery and due to expense and unknown potential side effects caused by the use of supraphysiological levels of growth factors, BMPs are used as a last-resort to heal recalcitrant fractures. Typical patient care also involves the administration of antibiotics, a narcotic, an NSAID, a COX-2 inhibitor or other pain killers during the healing process.

NSAIDs inhibit cyclooxygenase, thereby inhibiting the conversion of arachidonic acid into prostaglandins (PGD2, PGE2, PGF2α, PGI2, TXA2). Arachidonic acid is also a precursor for the leukotrienes (LTB4, LTC4, LTD4, LTE4), lipoxins (LXA4, LXB4), and 5-hydroxyeicosatetraenoic acid (5-HETE). The enzyme 5-lipoxygenase (5-LO) converts arachidonic acid to 5-hydroperoxyeicosatetraenoic acid (5-HpETE). This is the first step in the metabolic pathway which yields 5-HETE, the leulotrienes (LTs), and the lipoxins. Leukotrienes are also pro-inflammatory with the ability to attract neutrophils and cause capillary permeability. The arachidonic acid metabolic pathway is summarized in FIG. 1.

Lipoxygenases are nonheme iron-containing enzymes found in plants and animals that catalyze the oxygenation of certain polyunsaturated fatty acids, such as lipids and lipoproteins. Several lipoxygenase enzymes are known, each having a characteristic oxidation action. Mammalian lipoxygenases are named by the position in arachidonic acid that is oxygenated. For example, the enzyme 5-lipoxygenase converts arachidonic acid to 5-hydroperoxyeicosatetraenoic acid (5-HpETE), while the enzyme 12-lipoxygenas converts arachidonic acid to 12-HpETE. The activity of 5-lipoxygenase requires a co-factor commonly called FLAP (five lipoxygenase activating protein). Leukotriene synthesis is reduced by drugs that inhibit FLAP (MK866) or mice lacking FLAP.

WO 95/30419 discloses 5-LO inhibitors reduce osteoclast activity. The suppression of osteoclast activity inhibits bone resorption and reduces bone loss in human pathological conditions. Bone resorption is an integral part of fracture healing because it is necessary to remodel the newly formed bone into stronger, more mature bone. The inhibition of bone resorption would be expected to impair the later stages of normal fracture healing. Koivukalngas et al., *Long-term administration of clodronate does not prevent fracture healing in rats*. Clinical Orthopaedics and Related Research 408: 268-278 (2003) and Peter et al. *Effect of alendronate on fracture healing and bone remodeling in dogs*. Journal of Orthopaedic Research 14: 74-79 (1996) disclose the effects of bisphosphonate therapy on fracture healing. The data show that bisphosphonate therapy which impairs osteoclast activity and bone remodeling does not inhibit the initial stages of fracture repair but does impair the later bone remodeling stage. The bisphosphonate effect on fracture healing reveals itself as persistence of a large fracture callus that contains mechanically immature, woven bone rather than mechanically mature, lamellar bone.

WO 03/066048 discloses that 12/15-lipoxygenase inhibitors can be used to prevent bone loss or increase bone mass. The publication describes data showing that bone mineral density is preserved in transgenic mouse that overexpress IL-4 and that were treated with a 15-LO inhibitor. The publication does not disclose that 15-LO inhibitors can aid fracture healing or the treatment of non-unions.

Traianedes, K., et al., *5-Lipoxygenase metabolites inhibit bone formation in vitro*. Endocrinology, 139: 3178-3184 (1998) discloses the effects of LTB4,5-HETE, and LTD4 (all products of 5-LO function) on the differentiation of fetal rat calvaria (osteoblast) cells. The data show that 5-HETE and LTB4 reduce bone nodule formation and alkaline phosphatase activity in vitro but that LTD4 had no effect. The results from an in vitro organ culture model showed that LTB4 or 5-HETE treatment prevented a BMP2 induced increase in mouse calvaria thickness. The publication, however, does not disclose the use of any 5-LO inhibitors, nor does it disclose that 5-LO inhibition would lead to the same effect in cultured osteoblasts or in organ cultures. Similarly, Ren and Dziak, *Effects of leukotrienes on osteoblast cell proliferation*. Calcified Tissue International 49: 197-201 (1991) discloses that LTB4 treatment reduces proliferation of primary rat calvaria (osteoblast) cultures in vitro, but that LTB4 can promote proliferation of established osteoblast cell lines (Saos-2 and G292) in vitro at higher concentration (0.3-1 micromolar). Ren and Dziak also disclose that LTC4 had no effect on the proliferation of primary rat osteoblast cells or Saos-2 cells but did promote proliferation of G292 cells. Further, Ren and Dziak (disclose that treatment of Saos-2 cells with a 5-LO inhibitor (AA-861) had no effect on Saos-2 cell proliferation. The publication indicates that 5-LO inhibition should have no effect on osteogenesis.

Thus, it is readily apparent that compositions and methods for accelerating or enhancing bone formation or fracture healing would be highly desirable.

SUMMARY

The present invention provides methods of promoting osteogenesis by administering a compound that reduces a 5-lipoxygenase activity to treat a bone fracture, a bone defect or a condition treated by inducing bone formation.

In another aspect of the invention, the methods can further comprise an additional active agent such as a modulator of the activity of a cyclooxygenase. In one aspect the activity of a cyclooxygenase-2 (COX-2) is increased. In another aspect, the activity of cyclooxygenase-1 (COX-1) is reduced.

In one aspect, the methods use in vivo administration of a compound. In another aspect, ex vivo administration of a compound is used.

In one aspect, the compound is a small molecule. In another aspect the compound is an antisense compound. In another aspect, the compound is an RNAi compound.

These and other aspects of the present invention will become evident upon reference to the following detailed description and attached figures. In addition, various references are set forth herein which describe in more detail certain procedures or compositions, and are therefore incorporated by reference in their entirety.

BRIEF DESCRIPTION OF THE FIGURES

FIG. 2A represents the normal functioning of the pathway. FIG. 2B shows that the inhibition of COX-2 activity leads to excess leukotriene production which impairs bone formation in fracture healing or other osteogenic processes. FIG. 2C shows that the inhibition of lipoxygenase activity leads to excess prostaglandin production which accelerates or enhances bone formation in fracture repair or other osteogenic processes.

FIG. 6 shows that fracture healing is dramatically impaired in COX-2 knock-out mice and that the defect in healing occurs because of lack of osteogenesis (new bone formation). FIG. 6A shows data from x-rays and FIGS. 6B and 6C show the histological samples of 14-day old femur fractures in mice lacking a functional COX-1 gene. FIG. 6D shows data from x-rays and FIGS. 6E and 6F show the histological samples of 14-day old femur fractures in mice lacking a functional COX-2 gene.

FIG. 7 illustrates that osteogenesis is accelerated in rats treated with 5-LO inhibitors, resulting in fractures healing faster than in untreated rats.

FIG. 8 illustrates that osteogenesis is accelerated in rats treated with two different 5-LO inhibitors, resulting in fractures healing faster than in untreated rats. FIGS. 8A, 8B, and 8C show data from x-rays for vehicle control (8A), NDGA (8B), and AA-861 (8C).

DETAILED DESCRIPTION OF THE INVENTION

Figure 1:
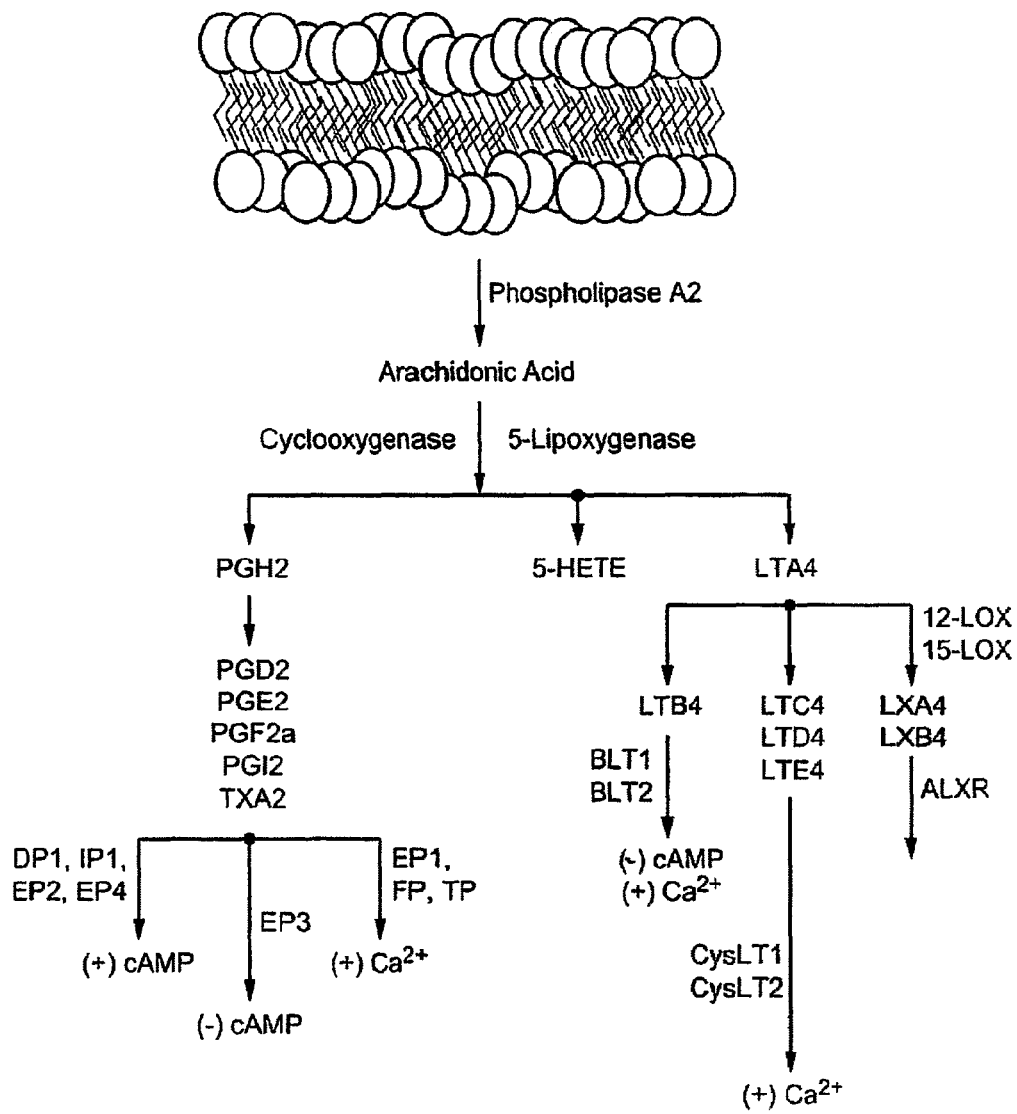
FIG. 1 summarizes an exemplary arachidonic acid metabolic or signaling pathway.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

All publications, patents and patent applications cited herein, whether supra or infra, are hereby incorporated by reference in their entirety.

I. Definitions

In describing the present invention, the following terms will be employed, and are intended to be defined as indicated below.

By "modulating an arachidonic acid metabolic or signaling pathway" is meant use of a drug or a compound which inhibits or promotes the activity or concentration of any enzyme or regulatory molecule involved in an arachidonic acid metabolism or signal pathway in a cell or animal. Preferably drug or a compound can be selected from a FLAP inhibitor such as BAYx 1005, NM-886, and MK-0591; a 5-Lipoxygenase inhibitor such as Zileuton, BAY-G576, RS-43,179, Wy-47, 288, ABT-761, vitamin A, and BWA4C; leukotriene receptor antagonists such as zafirlukast, montelukast, pranlukast, ICI-204,219, MK-571, MK-679, ONO-RS-411, SK&F 104,353, and Wy-48,252; a leukotriene B4 receptor antagonists; a leukotriene C4 synthase inhibitors; a Leukotriene A4 hydrolase inhibitors; a non-steroidal antiinflammatory drug (NSAOD), a leukotriene receptor antagonists and leukotriene analogs, compounds modulating the formation and action of leukotrienes, compounds that affect cyclooxygenase activity, compounds that affect prostaglandin activity such as receptor agonists or antagonists, prostaglandin analogs, compounds that affect leukotriene activity such as receptor agonists or antagonists, and leukotriene analogs.

By "accelerated" is meant that osteogenesis occurs more rapidly and the time required for bone healing is reduced, or the bone heals more quickly in a treated subject as compared to an untreated subject or a control subject.

By "enhancing" is meant that the healed bone in the treated subject has improved characteristics compared to an untreated subject, or a control subject such as, for example, greater bone strength.

By "fracture healing" or "fracture repair" is meant that, in particular, promoting the healing of bone fractures and bone defects, and improving the mechanical stability of the healing fracture or site. Such bone fractures may be, for example, the common, traumatic (disabling and non-osteoporotic) fractures, the osteoporotic fractures due to osteoporosis or osteopenia of any etiology, fractures due to Paget's disease or fractures due to bone loss as a consequence of side effects of other drugs, e.g. in patients receiving high doses of corticosteroids, fractures arising from other congenital or acquired disease such as, e.g., osteogenesis imperfecta and breast cancer, surgical created fractures (osteotomies) used for example in bone lengthening and limb lengthening procedures, and treatment of bone fracture delayed unions or non-unions. The invention augments fracture healing following normal reduction and immobilization of the fracture using techniques common to one skilled in the art by accelerating and enhancing bone formation.

By "bone formation" is meant that the rate of bone formation in a subject treated according to the methods of the invention, such as, e.g., by receiving a 5-lipoxygenase inhibitor, is increased over the bone formation rate in a subject that is not given a 5-lipoxygenase inhibitor. Such enhanced bone formation is determined herein using, e.g., quantitative digitized morphometry, as well as by other markers of bone formation, as described above. Bone formation is meant to include the osteogenic process used for spine fusions and other joint or bone ankylosis application, bone formation into or around prosthetic devices, or bone formation to augment existing bones or replace missing bones or bone segments.

By "osteogenesis" is meant the production of bone that is associated with repair of a fractured bone, repair of a bone that has a defect caused by intentional or non-intentional damage, or induction of bone formation used to fuse more than one bone or bone segment together. "Osteogenesis" is not meant to include bone formation associated with normal bone growth in adolescents. "Osteogenesis" also is not meant to include bone formation associated with normal bone homeostasis, which is often referred to as bone remodeling, in which bone is normally turned-over by a process whereby osteoclasts resorb bone and osteoblasts make new bone to replace that which has been resorbed.

By "bone defect" is meant damage to a bone such that a portion of the bone is removed or is otherwise missing. Such bone defects would include anomalous holes, gaps or openings created in the bone for purposes of a diagnostic or therapeutic procedure, loss of bone segments from trauma or disease, puncture wounds to the bone, and the like.

The term "modulating" refers to the effect of a modulator on an arachidonic acid metabolic or signaling pathway. A modulator can be, e.g., a polypeptide, nucleic acid, macromolecule, complex molecule, small molecule, compound, or the like (naturally occurring or non-naturally occurring) that is capable of causing modulation. Modulators can be evaluated for potential activity as inhibitors or activators (directly or indirectly) of a functional property, biological activity or process, or a combination thereof (e.g., agonist, partial antagonist, partial agonist, inverse agonist, antagonist, and the like), by inclusion in assays that measure the activity of an enzyme in the pathway.

The terms "effective amount" or "pharmaceutically effective amount" refer to a sufficient amount of an agent to provide the desired biological result. That result can be reduction and/or alleviation of the signs, symptoms, or causes of a disease, or any other desired alteration of a biological system. For example, an "effective amount" for therapeutic uses is the amount of the composition comprising an active compound herein required to provide a clinically significant increase in osteogenesis and, thus, healing rates in fracture repair; reversal of cartilage defects or disorders; stimulation and/or augmentation of bone formation in fracture non-unions, delayed unions and distraction osteogenesis; increase and/or acceleration of bone growth into prosthetic devices; enhanced or accelerated bone formation in joint ankylosis, bone ankylosis, or spine fusions, bone formation to augment existing bone or replace missing bone or bone segments such as during autograft, allograft, or synthetic bone material incorporation, and repair of dental defects.

As used herein, the terms "treat" or "treatment" are used interchangeably and are meant to indicate administering one or more compounds in accordance with the methods of the invention to promote osteogenesis to obtain a desired therapeutic objective. The terms further include ameliorating existing bone or cartilage deficit symptoms, preventing additional symptoms, ameliorating or preventing the underlying metabolic causes of symptoms, and/or encouraging bone growth.

As used herein, "small molecule" is meant to indicate a chemical compound having a molecular weight of less than about 500 daltons. Small molecules do not include biologic polymers such as polypeptides and polynucleotides.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

The compounds of the present invention may be used to inhibit or reduce the activity of 5-lipoxygenase, 5-lipoxygenase and cyclooxygenase, and other enzymes and compounds in an arachadonic acid metabolic or signaling pathway. In this context, inhibition and reduction of the enzyme activity refers to a lower level of measured activity relative to a control experiment in which the enzyme, cell, or subject is not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% or any amount between 10% and 100%, may be preferred for particular applications. Inhibition of enzyme activity may be through any mechanism, including, by way of example, but not limitation, a reduction in the amount of enzyme present, a competitive or non-competitive inhibition of catalytic activity, an interference with an interaction between the enzyme and a co-factor or accessory protein, etc. In addition, the compounds of the present invention may be used to increase a COX-2 activity. In particular embodiments, the increase of enzyme activity refers to a higher level of measured activity relative to a control experiment in which the enzyme, cell, or subject is not treated with the test compound. In particular embodiments, the increase in measured activity is at least a 10% increase. One of skill in the art will appreciate that an increase of the measured activity of at least 20%, 50%, 75%, 90% or 100% or any amount between 10% and 100% or beyond, may be preferred for particular applications. Increase of enzyme activity may be through any mechanism, including, by way of example but not limitation, an increase in the amount of enzyme present, or by increasing the enzyme's turnover rate, or altering its substrate binding properties.

References to the enzymes 5-lipoxygenase (5-LO), COX-1, and COX-2 are intended to encompass the exemplary sequences referenced in Table 1, some of which are provided immediately following Table 1, as well as sequences at least 90% identical, or at least 95%, or at least 96%, or at least 97%, or at least 98%, or at least 99% identical to the exemplary sequences as can be ascertained by one of ordinary skill using routine alignment algorithms such as e.g., BLAST. In addition, other mammalian homologues are encompassed. Such homologues are identified as such on the basis of e.g., sequence similarity, functional similarity, and by chromosome location. In addition to protein sequence, exemplary nucleic acid sequences are provided from which one of ordinary skill can readily obtain sequences of anti-sense and RNAi compounds useful for inhibiting the activity of the enzyme in accordance with the methods of the invention. Anti-sense compounds useful for practice of the invention are known in the art and can be obtained through commercial sources, as described in, e.g., Ding et al. (1999) BBRC Vol. 261, pp. 218-223 (incorporated by reference).

TABLE 1

Exemplary Sequences

| | Symbol | OMIM ID | Entre zGene ID | GeneBank Accession Number | mRNA (GenBank) | Protein (Swiss-Prot) | Similarity to human sequence |
|---|---|---|---|---|---|---|---|
| Name: arachidonate 5-lipoxygenase; aka: 5-LO, 5-lipoxygenase | | | | | | | |
| Human | ALOX5 | 152390 | 240 | NC_000010 | NM_000698 | P09917 | NA |
| Rat | Alox5 | NA | 25290 | NC_005103 | NM_012822 | P12527 | 86.29% ($n^1$) |
| | | | | | | | 92.94% ($p^2$) |
| Mouse | Alox5 | NA | 11689 | NC_000072 | NM_009662 | P48999 | 87.88% (n) |
| | | | | | | | 93.47% (p) |

TABLE 1-continued

Exemplary Sequences

| | Symbol | OMIM ID | EntrezGene ID | GeneBank Accession Number | mRNA (GenBank) | Protein (Swiss-Prot) | Similarity to human sequence |
|---|---|---|---|---|---|---|---|
| Name: arachidonate 5-lipoxygenase-activating protein; aka: FLAP | | | | | | | |
| Human | ALOX5AP | 603700 | 241 | NC_000013 | NM_001629 | P20292 | NA |
| Rat | Alox5ap | NA | 29624 | NC_005111 | NM_017260 | P20291 | 85.09% (n) 91.93% (p) |
| Mouse | Alox5ap | NA | 11690 | NC_000071 | NM_009663 | P30355 | 85.71% (n) 91.93% (p) |
| Name: prostaglandin-endoperoxide synthase 2; aka: cyclooxygenase-2, COX-2, PGHS-2 | | | | | | | |
| Human | PTGS2 | 600262 | 5743 | NC_000001 | NM_000963 | P35354 | NA |
| Rat | Ptgs2 | NA | 29527 | NC_005112 | NM_017232 | P35355 | 83.17% (n) 84.91% (p) |
| Mouse | Ptgs2 | NA | 19225 | NC_000067 | NM_011198 | Q05769 | 84.71% (n) 86.75% (p) |
| Name: prostaglandin-endoperoxide synthase 1; aka: cyclooxygenase-1, COX-1, PGHS-1 | | | | | | | |
| Human | PTGS1 | 176805 | 5742 | NC_000009 | NM_000962 | P23219 | NA |
| Rat | Ptgs1 | NA | 24693 | NC_005102 | NM_017043 | Q63921 | 84.87% (n) 88.11% (p) |
| Mouse | Ptgs1 | NA | 19224 | NC_000068 | NM_008969 | P22437 | 85.59% (n) 89.78% (p) |

[1]Similarity between mRNA sequences.
[2]Similarity between protein sequences.

```
Human 5-Lipoxygenase mRNA Sequence (GenBank RefSeq NM_000698)
                                                          (SEQ ID NO: 1)
   1 gccagggacc agtggtggga ggaggctgcg gcgctagatg cggacacctg gaccgccgcg 61 ccgaggctcc cggcgctcgc tgctcccgcg gcccgcgcca tgccctccta cacggtcacc 121 gtggccactg gcagccagtg gttcgccggc actgacgact acatctacct cagcctcgtg 181 ggctcggcgg gctgcagcga gaagcacctg ctggacaagc ccttctacaa cgacttcgag 241 cgtggcgcgg tggattcata cgacgtgact gtggacgagg aactgggcga gatccagctg 301 gtcagaatcg agaagcgcaa gtactggctg aatgacgact ggtacctgaa gtacatcacg 361 ctgaagacgc cccacgggga ctacatcgag ttcccctgct accgctggat caccggcgat 421 gtcgaggttg tcctgaggga tggacgcgca aagttggccc gagatgacca aattcacatt 481 ctcaagcaac accgacgtaa agaactggaa acacggcaaa acaatatcg atggatggag 541 tggaaccctg gcttcccctt gagcatcgat gccaaatgcc acaaggattt accccgtgat 601 atccagtttg atagtgaaaa aggagtggac tttgttctga attactccaa agcgatggag 661 aacctgttca tcaaccgctt catgcacatg ttccagtctt cttggaatga cttcgccgac 721 tttgagaaaa tcttgtcaa gatcagcaac actatttctg agcgggtcat gaatcactgg 781 caggaagacc tgatgtttgg ctaccagttc ctgaatggct gcaaccctgt gttgatccgg 841 cgctgcacag agctgcccga gaagctcccg gtgaccacgg agatggtaga gtgcagcctg 901 gagcggcagc tcagcttgga gcaggaggtc cagcaaggga acattttcat cgtggacttt 961 gagctgctgc atggcatcga tgccaacaaa acagacccct gcacactcca gttcctggcc 1021 gctcccatct gcttgctgta taagaacctg gccaacaaga ttgtccccat gccatccag 1081 ctcaaccaaa tccgggaga tgagaaccct atttttcctcc cttcggatgc aaaatacgac 1141 tggcttttgg ccaaaatctg ggtgcgttcc agtgacttcc acgtccacca gaccatcacc 1201 caccttctgc gaacacatct ggtgtctgag gtttttggca ttgcaatgta ccgccagctg 1261 cctgctgtgc accccatttt caagctgctg gtggcacacg tgagattcac cattgcaatc
```

-continued

```
1321 aacaccaagg cccgtgagca gctcatctgc gagtgtggcc tctttgacaa ggccaacgcc
1381 acaggggcg gtgggcacgt gcagatggtg cagagggcca tgaaggacat gacctatgcc
1441 tccctgtgct ttcccgaggc catcaaggcc cggggcatgg agagcaaaga agacatcccc
1501 tactacttct accgggacga cgggctcctg gtgtgggaag ccatcaggac gttcacggcc
1561 gaggtggtag acatctacta cgagggcgac caggtggtgg aggaygaccc ggagctgcag
1621 gacttcgtga acgatgtcta cgtgtacggc atgcgggggcc gcaagtcctc aggcttcccc
1681 aagtcggtca agagccggga gcagctgtcg gagtacctga ccgtggtgat cttcaccgcc
1741 tccgcccagc acgccgcggt caacttcggc cagtacgact ggtgctcctg gatccccaat
1801 gcgcccccaa ccatgcgagc cccgccaccg actgccaagg gcgtggtgac cattgagcag
1861 atcgtggaca cgctgcccga ccgcggccgc tcctgctggc atctgggtgc agtgtgggcg
1921 ctgagccagt tccaggaaaa cgagctgttc ctgggcatgt acccagaaga gcattttatc
1981 gagaagcctg tgaaggaagc catggcccga ttccgcaaga acctcgaggc cattgtcagc
2041 gtgattgctg agcgcaacaa gaagaagcag ctgccatatt actacttgtc cccagaccgg
2101 attccgaaca gtgtggccat ctgagcacac tgccagtctc actgtgggaa ggccagctgc
2161 cccagccaga tggactccag cctgcctggc aggctgtctg gccaggcctc ttggcagtca
2221 catctcttca tccgaggcca gtacctttcc atttattctt tgatcttcag ggaactgcat
2281 agattgatca aagtgtaaac accatagggga cccattatac acagagcagg actgcacagc
2341 gtcctgtcca cacccagctc agcatttcca caccaagcag caacagcaaa tcacgaccac
2401 tgatagatgt ctattcttgt tggagacatg ggatgattat tttctgttct atttgtgctt
2461 agtccaattc cttgcacata gtaggtaccc aattcaatta ctattgaatg aattaagaat
2521 tggttgccat aaaaataaat cagttcattt aaaaaaaaaa aaaaaaa
```

Human 5-Lipoxygenase Protein Sequence (GenBank RefSeq NM_000698)

(SEQ ID NO: 2)

MPSYTVTVATGSQWFAGTDDYIYLSLVGSAGCSEKHLLDKPFYNDFERGAVDSYDVTVDEELGEIQLVRIEKRKY
WLNDDWYLKYITLKTPHGDYIEFPCYRWITGDVEVVLRDGRAKLARDDQIHILKQHRRKELETRQKQYRWMEWNP
GFPLSIDAKCHKDLPRKIQFDSEKGVDFVLNYSKAMENLFINRFMHMFQSSWNDFADFEKIFVKISNTISERVMN
HWQEDLMFGYQFLNGCNPVLIRRCTELPEKLPVTTEMVECSLERQLSLEQEVQQGNIFIVDFELLDGIDANKTDP
CTLQFLAAPICLLYKNLANKIVPIAIQLNQIPGDENPIFLPSDAKYDWLLAKIWVRSSDFHVHQTITHLLRTHLV
SEVFGIAMYRQLPAVHPIFKLLVAHVRFTIAINTKAREQLICECGLFDKANATGGGHVQMVQRAMKDLTYASLC
FPEAIKARGMESKEDIPYYFYRDDGLLVWEAIRTFTAEVVDIYYEGDQVVEEDPELQDFVNDVYVYGMRGRKSSG
FPKSVKSREQLSEYLTVVIFTASAQHAAVNFGQYDWCSWIPNAPPTMRAPPPTAKGVVTIEQIVDTLPDRGRSCW
HLGAVWALSQFQENELFLGMYPEEHFIEKPVKEAMARFRKNLEAIVSVIAERNKKKQLPYYYLSPDRIPNSVAI

Human FLAP mRNA Sequence (GenBank RefSeq NM_001629)

(SEQ ID NO: 3)

```
  1 acttcccctt cctgtacagg gcaggttgtg cagctggagg cagagcagtc ctctctgggg
 61 agcctgaagc aaacatggat caagaaactg taggcaatgt tgtcctgttg gccatcgtca
121 ccctcatcag cgtggtccag aatggattct ttgcccataa agtggagcac gaaagcagga
181 cccagaatgg gaggagcttc agaggaccg gaacacttgc ctttgagcgg gtctacactg
241 ccaaccagaa ctgtgtagat gcgtacccca cttctcctcgc tgtgctctgg tctgcggggc
301 tactttgcag ccaagttcct gctgcgtttg ctggactgat gtacttgttt gtgaggcaaa
361 agtactttgt cggttaccta ggagagagaa cgcagagcac ccctggctac atatttggga
421 aacgcatcat actcttcctg ttcctcatgt ccgttgctgg catattcaac tattacctca
```

```
481 tcttctttt cggaagtgac tttgaaaact acataaagac gatctccacc accatctccc 541 ctctacttct cattccctaa ctctctgctg aatatggggt tggtgttctc atctaatcaa 601 tacctacaag tcatcataat tcagctcttg agagcattct gctcttcttt agatggctgt 661 aaatctattg gccatctggg cttcacagct tgagttaacc ttgcttttcc gggaacaaaa 721 tgatgtcatg tcagctccgc cccttgaaca tgaccgtggc cccaaatttg ctattcccat 781 gcattttgtt tgtttcttca cttatcct9t tctctgaaga tgttttgtga ccaggtttgt 841 gttttcttaa aataaaatgc agagacatgt ttt
```

Human FLAP Protein Sequence (GenBank RefSeq NM_001629)
(SEQ ID NO: 4)

MDQETVGNVVLLAIVTLISVVQNGFFAHKVEHESRTQNGRSFQRTGTLAFERVYTANQNCVDAYPTFLAVLWSAG

LLCSQVPAAFAGLMYLFVRQKYFVGYLGERTQSTPGYIFGKRIILFLFLMSVAGIFNYYLIFFFGSDFENYIKTI

STTISPLLLIP

Human COX-2 mRNA Sequence (GenBank RefSeq NM_00963)
(SEQ ID NO: 5)
```
  1 caattgtcat acgacttgca gtgagcgtca ggagcacgtc caggaactcc tcagcagcgc 61 ctccttcagc tccacagcca gacgccctca gacagcaaag cctaccccg cgccgcgccc 121 tgcccgccgc tcggatgctc gcccgcgccc tgctgctgtg cgcggtcctg gcgctcagcc 181 atacagcaaa tccttgctgt tcccacccat gtcaaaaccg aggtgtatgt atgagtgtgg 241 gatttgacca gtataagtgc gattgtaccc ggacaggatt ctatggagaa aactgctcaa 301 caccggaatt tttgacaaga ataaaattat ttctgaaacc cactccaaac acagtgcact 361 acatacttac ccacttcaag ggattttgga acgttgtgaa taacattccc ttccttcgaa 421 atgcaattat gagttatgtc ttgacatcca gatcacattt gattgacagt ccaccaactt 481 acaatgctga ctatggctac aaaagctggg aagccttctc taacctctcc tattatacta 541 gagcccttcc tcct9tgcct gatgattgcc cgactccctt gggtgtcaaa ggtaaaaagc 601 agcttcctga ttcaaatgag attgtggaaa aattgcttct aagaagaaag ttcatccctg 661 atccccaggg ctcaaacatg atgtttgcat tctttgccca gcacttcacg catcagtttt 721 tcaagacaga tcataagcga gggccagctt tcaccaacgg ctgggccat ggggtggact 781 taaatcatat ttacggtgaa actctggcta gacagcgtaa actgcgcctt tcaaggatg 841 gaaaaatgaa atatcagata attgatggag agatgtatcc tcccacagtc aaagatactc 901 aggcagagat gatctaccct cctcaagtcc ctgagcatct acggtttgct gtggggcagg 961 aggtcttttgg tctggtgcct ggtctgatga tgtatgccac aatctggctg cgggaacaca 1021 acagagtatg cgatgtgctt aaacaggagc atcctgaatg gggtgatgag cagttgttcc 1081 agacaagcag gctaatactg ataggagaga ctattaagat tgtgattgaa gattatgtgc 1141 aacacttgag tggctatcac ttcaaactga aatttgaccc agaactactt ttcaacaaac 1201 aattccagta ccaaaatcgt attgctgctg aatttaacac cctctatcac tggcatccc 1261 ttctgcctga cacctttcaa attcatgacc agaaatacaa ctatcaacag tttatctaca 1321 acaactctat attgctggaa catggaatta cccagtttgt tgaatcatta accaggcaaa 1381 ttgctggcag ggttgctggt ggtaggaatg ttccacccgc agtacagaaa gtatcacagg 1441 cttccattga ccagagcagg cagatgaaat accagtcttt taatgagtac cgcaaacgct 1501 ttatgctgaa gccctatgaa tcatttgaag aacttacagg agaaaaggaa atgtctgcag 1561 agttggaagc actctatggt gacatcgatg ctgtggagct gtatcctgcc cttctggtag 1621 aaaagcctcg gccagatgcc atctttggtg aaaccatggt agaagttgga gcaccattct
```

-continued

```
1681 ccttgaaagg acttatgggt aatgttatat gttctcctgc ctactggaag ccaagcactt
1741 ttggtggaga agtgggtttt caaatcatca acactgcctc aattcagtct ctcatctgca
1801 ataacgtgaa gggctgtccc tttacttcat tcagtgttcc agatccagag ctcattaaaa
1861 cagtcaccat caatgcaagt tcttcccgct ccggactaga tgatatcaat cccacagtac
1921 tactaaaaga acgttcgact gaactgtaga agtctaatga tcatatttat ttatttatat
1981 gaaccatgtc tattaattta attatttaat aatatttata ttaaactcct tatgttactt
2041 aacatcttct gtaacagaag tcagtactcc tgttgcggag aaaggagtca tacttgtgaa
2101 gacttttatg tcactactct aaagattttg ctgttgctgt taagtttgga aaacagtttt
2161 tattctgttt tataaaccag agagaaatga gttttgacgt ctttttactt gaatttcaac
2221 ttatattata agaacgaaag taaagatgtt tgaatactta aacactatca caagatggca
2281 aaatgctgaa agttttttaca ctgtcgatgt ttccaatgca tcttacatga tgcattagaa
2341 gtaactaatg tttgaaattt taaagtactt ttggttattt ttctgtcatc aaacaaaaac
2401 aggtatcagt gcattattaa atgaatattt aaattagaca ttaccagtaa tttcatgtct
2461 acttttttaaa atcagcaatg aaacaataat ttgaaatttc taaattcata gggtagaatc
2521 acctgtaaaa gcttgtttga tttcttaaag ttattaaact tgtacatata ccaaaaagaa
2581 gctgtcttgg atttaaatct gtaaaatcag atgaaatttt actacaattg cttgttaaaa
2641 tattttataa gtgatgttcc ttttttcacca agagtataaa cctttttagt gtgactgtta
2701 aaacttcctt ttaaatcaaa atgccaaatt tattaaggtg gtggagccac tgcagtgtta
2761 tctcaaaata agaatatttt gttgagatat tccagaattt gtttatatgg ctggtaacat
2821 gtaaaatcta tatcagcaaa agggtctacc tttaaaataa gcaataacaa agaagaaaac
2881 caaattattg ttcaaattta ggtttaaact tttgaagcaa acttttttttt atccttgtgc
2941 actgcaggcc tggtactcag atttttgctat gaggttaatg aagtaccaag ctgtgcttga
3001 ataacgatat gttttctcag atttttctgtt gtacagttta atttagcagt ccatatcaca
3061 ttgcaaaagt agcaatgacc taataaaata cctcttcaaa atgcttaaat tcatttcaca
3121 cattaatttt atctcagtct tgaagccaat tcagtaggtg cattggaatc aagcctggct
3181 acctgcatgc tgttcctttt cttttcttct tttagccatt ttgctaagag acacagtctt
3241 ctcatcactt cgtttctcct attttgtttt actagtttta agatcagagt tcactttctt
3301 tggactctgc ctatattttc ttacctgaac ttttgcaagt tttcaggtaa acctcagctc
3361 aggactgcta tttagctcct cttaagaaga ttaaaagaga aaaaaaaagg cccttttaaa
3421 aatagtatac acttatttta agtgaaaagc agagaatttt atttatagct aattttagct
3481 atctgtaacc aagatggatg caaagaggct agtgcatcag agagaactgt acggggtttg
3541 tgactggaaa aagttacgtt cccattctaa ttaatgccct ttcttattta aaaacaaaac
3601 caaatgatat ctaagtagtt ctcagcaata ataataatga cgataatact tcttttccac
3661 atctcattgt cactgacatt taatggtact gtatattact taatttattg aagattatta
3721 tttatgtctt attaggacac tatggttata aactgtgttt aagcctacaa tcattgattt
3781 ttttttgtta tgtcacaatc agtatatttt ctttggggtt acctctctga atattatgta
3841 aacaatccaa agaaatgatt gtattaagat ttgtgaataa attttttagaa atctgattgg
3901 catattgaga tatttaaggt tgaatgtttg tccttaggat aggcctatgt gatagcccac
3961 aaagaatatt gtctcattag cctgaatgtg ccataagact gaccttttaa aatgttttga
4021 gggatctgtg gatgcttcgt taatttgttc agccacaatt tattgagaaa atattctgtg
```

```
4081 tcaagcactg tgggttttaa tatttttaaa tcaaacgctg attacagata atagtattta
4141 tataaataat tgaaaaaaat tttcttttgg gaagagggag aaaatgaaat aaatatcatt
4201 aaagataact caggagaatc ttctttacaa ttttacgttt agaatgttta aggttaagaa
4261 agaaatagtc aatatgcttg tataaaacac tgttcactgt ttttttaaa aaaaaaactt
4321 gatttgttat taacattgat ctgctgacaa aacctgggaa tttgggttgt gtatgcgaat
4381 gtttcagtgc ctcagacaaa tgtgtattta acttatgtaa aagataagtc tggaaataaa
4441 tgtctgttta tttttgtact attta
```

Human COX2 Protein Sequence (GenBank RefSeq NM_000963)

(SEQ ID NO: 6)

MLARALLLCAVLALSHTANPCCSHPCQNRGVCMSVGFDQYKCDCTRTGFYGENCSTPEFLTRIKLFLKPTPNTVH
YILTHFKGFWNVVNNIPFLRNAIMSYVLTSRSHLIDSPPTYNADYGYKSWEAFSNLSYYTRALPPVPDDCPTPLG
VKGKKQLPDSNEIVEKLLLRRKFIPDPQGSNMMFAFFAQHFTHQFFKTDHKRGPAFTNGLGHGVDLNHIYGETLA
RQRKLRLFKDGKMKYQIIDGEMYPPTVKDTQAEMIYPPQVPEHLRFAVGQEVFGLVPGLMMYATIWLREHNRVCD
VLKQEHPEWGDEQLFQTSRLILIGETIKIVIEDYVQHLSGYHFKLKFDPELLFNKQFQYQNRIAAEFNTLYHWHP
LLPDTFQIHDQKYNYQQFIYNNSILLEHGITQFVESFTRQIAGRVAGGRNVPPAVQKVSQASIDQSRQMKYQSFN
EYRKRFMLKPYESFEELTGEKEMSAELEALYGDIDAVELYPALLVEKPRPDAIFGETMVEVGAPFSLKGLNGNVI
CSPAYWKPSTFGGEVGFQIINTASIQSLICNNVKGCPFTSFSVPDPELIKTVTINASSSRSGLDDINPTVLLKER
STEL

Human COX-1 mRNA Sequence (GenBank Refseq NM_000962)

(SEQ ID NO: 7)

```
   1 aggtgacagc tggagggagg agcggggtg gagccggggg aagggtgggg aggggatggg
  61 ctggagctcc gggcagtgtg cgaggcgcac gcacaggagc ctgcactctg cgtcccgcac
 121 cccagcagcc gcgccatgag ccggagtctc ttgctctggt tcttgctgtt cctgctcctg
 181 ctcccgccgc tccccgtcct gctcgcggac ccaggggcgc ccacgccagt gaatccctgt
 241 tgttactatc catgccagca ccagggcatc tgtgtccgct tcggccttga ccgctaccag
 301 tgtgactgca cccgcacggg ctattccggc cccaactgca ccatccctgg cctgtggacc
 361 tggctccgga attcactgcg gcccagcccc tctttcaccc acttcctgct cactcacggg
 421 cgctggttct gggagtttgt caatgccacc ttcatccgag agatgctcat gcgcctggta
 481 ctcacagtgc gctccaacct tatccccagt cccccccacct acaactcagc acatgactac
 541 atcagctggg agtctttctc caacgtgagc tattacactc gtattctgcc ctctgtgcct
 601 aaagattgcc ccacacccat gggaaccaaa gggaagaagc agttgccaga tgcccagctc
 661 ctggcccgcc gcttcctgct caggaggaag ttcatacctg accccaagg caccaacctc
 721 atgtttgcct tctttgcaca acacttcacc caccagttct caaaacttc tggcaagatg
 781 ggtcctggct tcaccaaggc cttgggccat ggggtagacc tcggccacat ttatggagac
 841 aatctgagc gtcagtatca actgcggctc tttaaggatg ggaaactaaa gtaccaggtg
 901 ctggatggag aaatgtaccc gccctcggta gaagaggcgc ctgtgttgat gcactacccc
 961 cgaggcatcc cgcccagag ccagatggct gtggcaggg aggtgtttgg gctgcttcct
1021 gggctcatgc tgtatgccac gctctggcta cytgagcaca accgtgtgtg tgacctgctg
1081 aaggctgagc accccacctg gggcgatgag cagcttttc agacgacccg cctcatcctc
1141 ataggggaga ccatcaagat tgtcatcgag gagtacgtgc agcagctgag tggctatttc
1201 ctgcagctga aatttgaccc agagctgctg ttcggtgtcc agttccaata ccgcaaccgc
1261 attgccatgg agttcaacca tctctaccac tggcaccccc tcatgcctga ctccttcaag
```

-continued

```
1321 gtgggctccc aggagtacag ctacgagcag ttcttgttca acacctccat gttggtggac
1381 tatggggttg aggccctggt ggatgccttc tctcgccaga ttgctggccg gatcggtggg
1441 ggcaggaaca tggaccacca catcctgcat gtggctgtgg atgtcatcag ggagtctcgg
1501 gagatgcggc tgcagcccct caatgagtac cgcaagaggt ttggcatgaa accctacacc
1561 tccttccagg agctcgtagg agagaaggag atggcagcag agttggagga attgtatgga
1621 gacattgatg cgttggagtt ctaccctgga ctgcttcttg aaaagtgcca tccaaactct
1681 atctttgggg agagtatgat agagattggg gctccctttt ccctcaaggg tctcctaggg
1741 aatcccatct gttctccgga gtactggaag ccgagcacat ttggcggcga ggtgggcttt
1801 aacattgtca agacggccac actgaagaag ctggtctgcc tcaacaccaa gacctgtccc
1861 tacgtttcct tccgtgtgcc ggatgccagt caggatgatg gcctgctgt ggagcgacca
1921 tccacagagc tctgaggggc aggaaagcag cattctggag gggagagctt tgtgcttgtc
1981 attccagagt gctgaggcca gggctgatgg tcttaaatgc tcattttctg gtttggcatg
2041 gtgagtgttg ggttgacat ttagaacttt aagtctcacc cattatctgg aatattgtga
2101 ttctgtttat tcttccagaa tgctgaactc cttgttagcc cttcagattg ttaggagtgg
2161 ttctcatttg gtctgccaga atactgggtt cttagttgac aacctagaat gtcagatttc
2221 tggttgattt gtaacacagt cattctagga tgtggagcta ctgatgaaat ctgctagaaa
2281 gttagggggt tcttatttg cattccagaa tcttgacttt ctgattggtg attcaaagtg
2341 ttgtgttcct ggctgatgat ccagaacagt ggctcgtatc ccaaatctgt cagcatctgg
2401 ctgtctagaa tgtggatttg attcattttc ctgttcagtg agatatcata gagacggaga
2461 tcctaaggtc caacaagaat gcattccctg aatctgtgcc tgcactgaga gggcaaggaa
2521 gtggggtgtt cttcttggga cccccactaa gaccctggtc tgaggatgta gagagaacag
2581 gtgggctgta ttcacgccat tggttggaag ctaccagagc tctatcccca tccaggtctt
2641 gactcatggc agctgtttct catgaagcta ataaaattcg ctttctaaag ttacctgtta
2701 tatatctctt ttggtcccat cctctaaagc agaggcaaca ctggaacatg gctagtcttt
2761 cttgtagcca tggctgggcg tgctagaggt tgcagcatga gactttctgc tgggatcctt
2821 gggcccatca ctgtatagac atgctaccac tggtacttcc tttctccctg cgggccaggc
2881 actgcccttt tcaggaagct ctcttaaaat acccattgcc ccagacctgg aagatataac
2941 attcagttcc caccatctga ttaaaacaac ttcctcccct acagagcata caacagaggg
3001 ggcacccggg gaggagagca catactgtgt tccaatttca cgcttttaat tctcatttgt
3061 tctcacacca acagtgtgaa gtgcgtggta taatctccat ttcaaaacca aggaagcagc
3121 ctcagagtgg tcgagtgaca cacctcacgc aggctgagtc cagagcttgt gctcctcttg
3181 attcctggtt tgactcagtt ccaggcctga tcttgcctgt ctggctcagg gtcaaagaca
3241 gaatggtgga gtgtagcctc cacctgatat tcaggctact cattcagtcc caaatatgta
3301 ttttcctaag tgtttactat gtgccagttc ctgtaacagg tgtggggaca cagaagtgag
3361 taatcaatac agacaaggtt ctgcccttat ggagctcaca ctccagtggc agacasacag
3421 accataaata aggaaacgat gaaataagat atatacaagg tgagtgtgac ttcccttcta
3481 accccctctg ctctgtcctc ccctattgcg ctctcaagac cagagaccca acagcagtga
3541 tctcagggca gacagccctc cactccagct ctgagaccct tttctcagga cctctgtagg
3601 cagcagagag agaggacaga gggtaagat gaggggttga gggaaggttc ttcatgatcc
3661 acactttggg cttagtattt ctcaggaaga gctatggccc agaaacaaca ggggaaacta
```

-continued

```
3721 gagttcggtc tgacagtcct tggggttaag tctcctgtct tatggtccag aaactcctgt 3781 ttctccttag ttggctggaa actgctccca tcattccttc tggcctctgc tgaatgcagg 3841 gaatgcaatc cttccctgct cttgcagttg ctctgacgta gaaagatcct tcgggtgctg 3901 gaagtctcca tgaagagctt gtgtcctgtc ctttcttgca gattctattt ccctcttct 3961 gctaatacct cttactttgc ttgagaatcc tctcctttct tattaatttc agtcttggtg 4021 gttctatcag gggtgcattc tggccaaggg gtgggcctgt gaatcaatcc tgggcaatca 4081 gacaccctct ccttaaaaac tggcccgtgg agactgagat cactgactct gactcatccc 4141 cacagctggc tctgacaaga tggtccattt gttcctgctt ccgagataca cagggcagcc 4201 tggatccctg cccttctcaa gactttagct tttccttcca tccggtggcc tattccagga 4261 attcctcttt tgcttaaatc agttggagtt tgtgtctgtt gcttgtaatc aagcctttat 4321 ggctgctggg ctgagtgaca caagcacttt aatggcctgg agggactttt aatcagtgaa 4381 gatgcaatca gacaagtgtt ttggaaagag caccctcgag aagggtggat gacagggcag 4441 agcaggaagg acaggaagct ggcagaacgg aggaggctgc agccgtggtc caaccaggag 4501 ctgatgggca ctggggctag gggaagggct ttgagggtgg aaggatggga tgggttccag 4561 aggtattcct ctcttaaatg caagtgccta gattaggtag actttgctta gtattgacaa 4621 ctgcacatga aagttttgca aagggaaaca ggctaaatgc accaagaaag cttcttcaga 4681 gtgaagaatc ttaatgcttg taatttaaac atttgttcct ggagttttga tttggtggat 4741 gtgatggttg gttttatttg tcagtttggt tgggctatag cacacagtta tttaatcaaa 4801 cagtaatcta ggtgtggctg tgaaggtatt ttgtagatgt gattaacatc tacaatcagt 4861 tgactttaag tgaaagagat tacttaaata atttgggtga gctgcacctg attagttgaa 4921 aggcctcaag aacaaacact gcagtttcct ggaaaagaag aaactttgcc tcaagactat 4981 agccatcgac tcctgcctga gtttccagcc tgctagtctg ccctatggat ttgaagtttg 5041 ccaaccccaa caattgtgtg aattaatttc taaaaataaa gctatataca gcc
```

Human COX1 Protein Sequence (GenBank RefSeq NM_000962)
(SEQ ID NO: 8)

MSRSLLLWFLLFLLLLPPLPVLLADPGAPTPVNPCCYYPCQHQGICVRFGLDRYQCDCTRTGYSGPNCTIPGLWT

WLRNSLRPSPSFTHFLLTHGRWFWEFVNATFIREMLMRLVLTVRSNLIPSPPTYNSAHDYISWESFSNVSYYTRI

LPSVPKDCPTPMGTKGKKQLPDAQLLARRFLLRRKFIPDPQGTNLMFAFFAQHFTHQFFKTSGKMGPGFTKALGH

GVDLGHIYGDNLERQYQLRLFKDGKLKYQVLDGEMYPPSVEEAPVLMHYPRGIPPQSQMAVGQEVFGLLPGLMLY

ATLWLREHNRVCDLLKAEHPTWGDEQLFQTTRLILIGETIKIVIEEYVQQLSGYFLQLKFDPELLFGVQFQYRNR

IAMEFNHLYHWHPLMPDSFKVGSQEYSYEQFLFNTSMLVDYGVEALVDAFSRQIAGRIGGGRNMDHHILHVAVDV

IRESREMRLQPFNEYRKRFGMKPYTSFQELVGEKEMAAELEELYGDIDALEFYPGLLLEKCHPNSIFGESMIEIG

APFSLKGLLGNPICSPEYWKPSTFGGEVGFNIVKTATLKKLVCLNTKTCPYVSFRVPDASQDDGPAVERPSTEL

II. 5-Lipoxygenase Inhibitors

Figure 2:
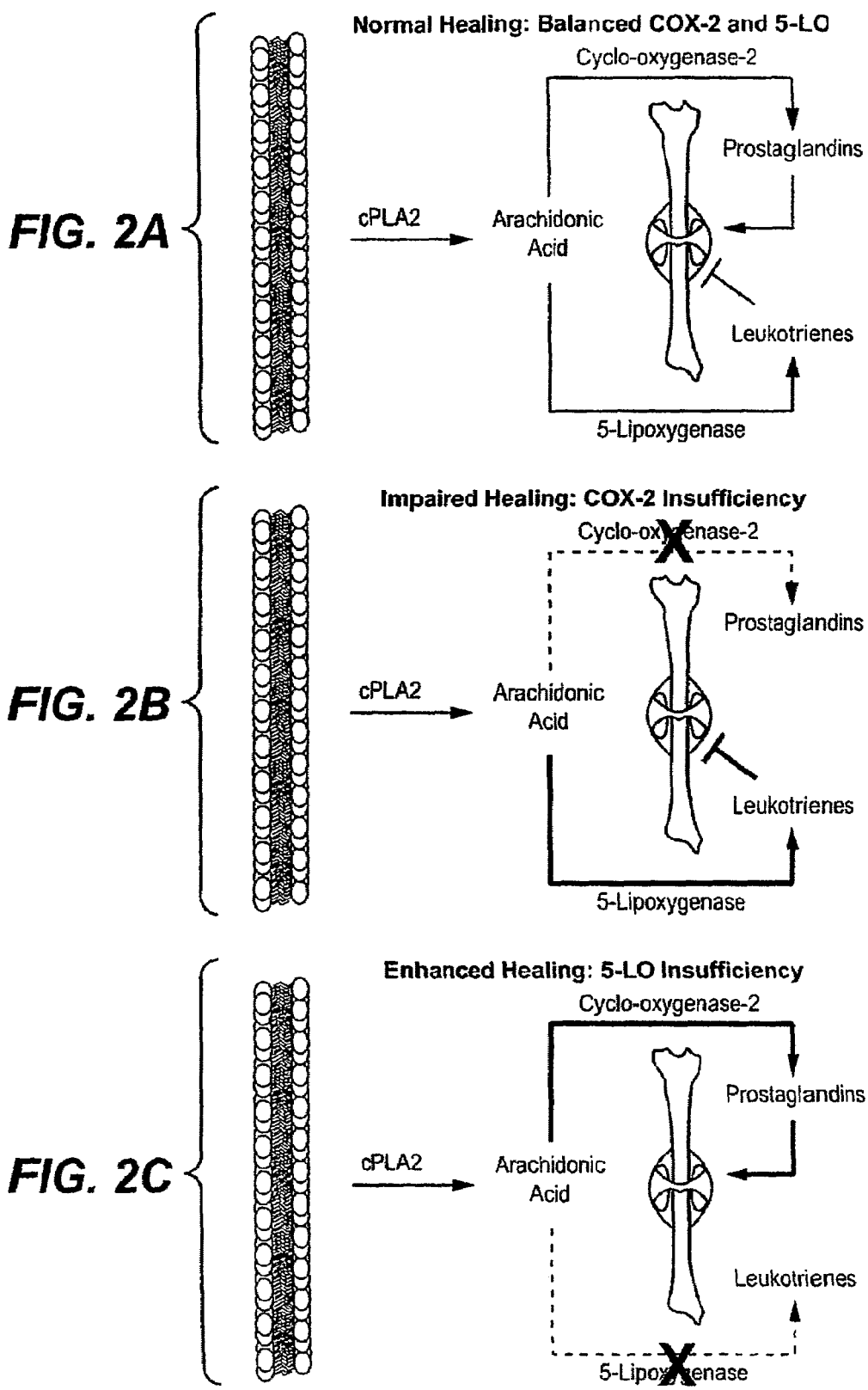
FIG. 2 illustrates the modulation of arachidonic acid metabolism by altering cyclooxygenase activity or lipoxygenase activity to accelerate or enhance bone formation.

The applicant has discovered that inhibiting the activity of 5-lipoxygenase promotes osteogenesis which can be used to accelerate and/or enhance the healing of a bone fracture, to treat a bone defect, or to treat by inducing bone formation. The applicant's discovery is based on his hypothesis that a potential mechanism by which loss of COX-2 function could inhibit fracture healing was by shunting arachidonic acid into the lipoxygenase pathway with consequent formation of abnormally high inhibitory 5-HETE, LTB4, or other 5-LO metabolite levels (FIG. 2). During a normal inflammation response, such as a fracture, the synthesis of prostaglandins and leukotrienes is balanced (FIG. 2A). Without being bound to a theory, the inventor theorizes that inhibiting COX-2 function shunts arachidonic acid into the lipoxygenase pathway to produce excess leukotrienes thereby impairing bone formation (FIG. 2B). Conversely, by inhibiting 5-lipoxygenase activity, arachidonic acid is shunted into the cyclooxygenase pathway to produce excess prostaglandins that accelerate or enhance bone formation (FIG. 2C).

Figure 3:
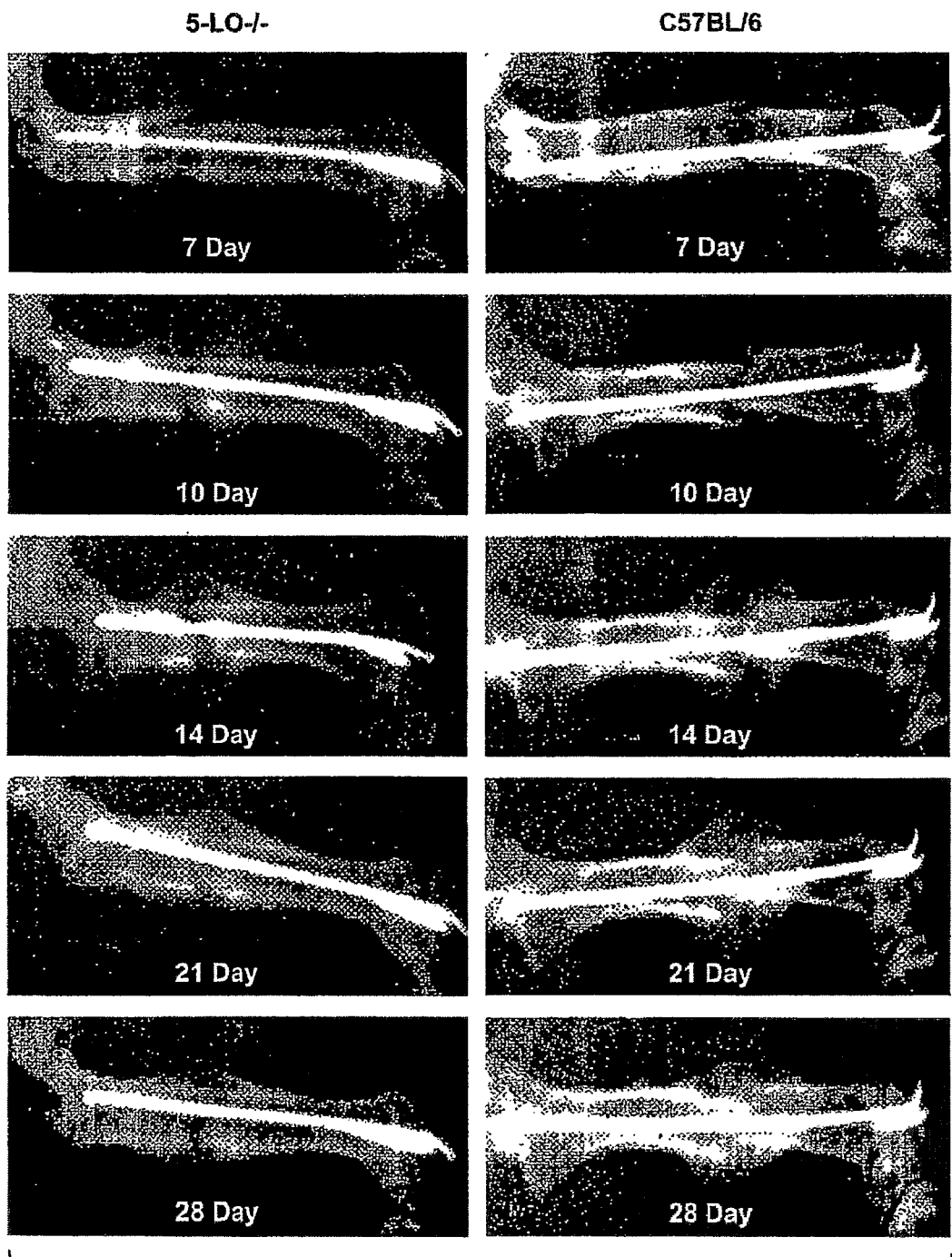
FIG. 3 shows that serial x-rays of femur fractures made from a 5LO-/- mouse and a normal mouse (C57BL/6). The x-rays show that osteogenesis, and therefore fracture healing is accelerated in the 5LO-/- mouse.
Figure 4A:
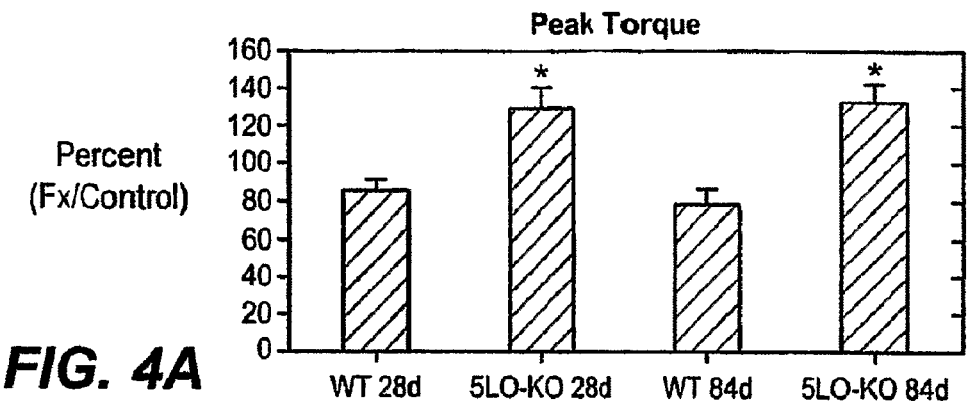
FIG. 4 illustrates mechanical testing data of fracture healing in wild-type (WT) and 5-LO knockout mice (5LO-KO or 5-LO-/-) 28 days and 84 days after the onset of the fracture. Peak torque (FIG. 4A), rigidity (FIG. 4B), maximum shear stress (FIG. 4C), and shear modulus (FIG. 4D) were calculated from callus dimensions and the torque to angular displacement curves.
Figure 4B:
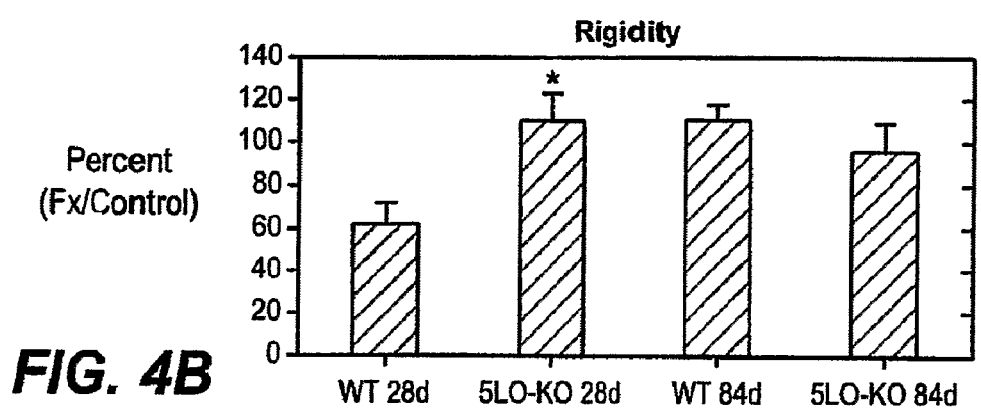
Figure 4C:
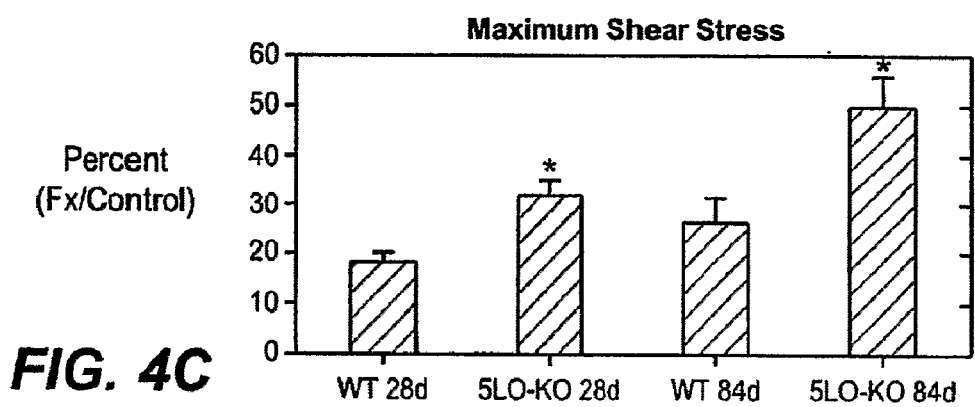
Figure 4D:
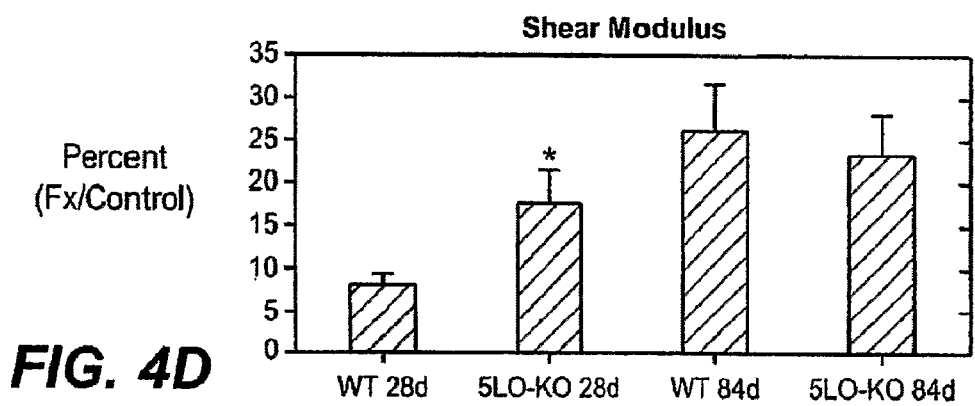

To test this potential mechanism, fracture healing was assessed in 5-LO−/− mice. The applicant found that loss of 5-LO function accelerates healing. Radiographic examination of fracture healing in age-matched mice in the C57BL/6 background showed that fracture bridging occurred by 2 weeks post-fracture in the 5-LO-/- mice as compared to 3 weeks post-fracture in the normal mice (FIG. 3). Further, callus remodeling was significantly accelerated, thus the 5-LO-/- callus regains its initial structural and material properties much faster than in normal mice based upon torsional mechanical testing (FIG. 4 and TABLE 2). Thus, loss of 5-LO function accelerates and enhances fracture healing and bone formation.

Figure 5:
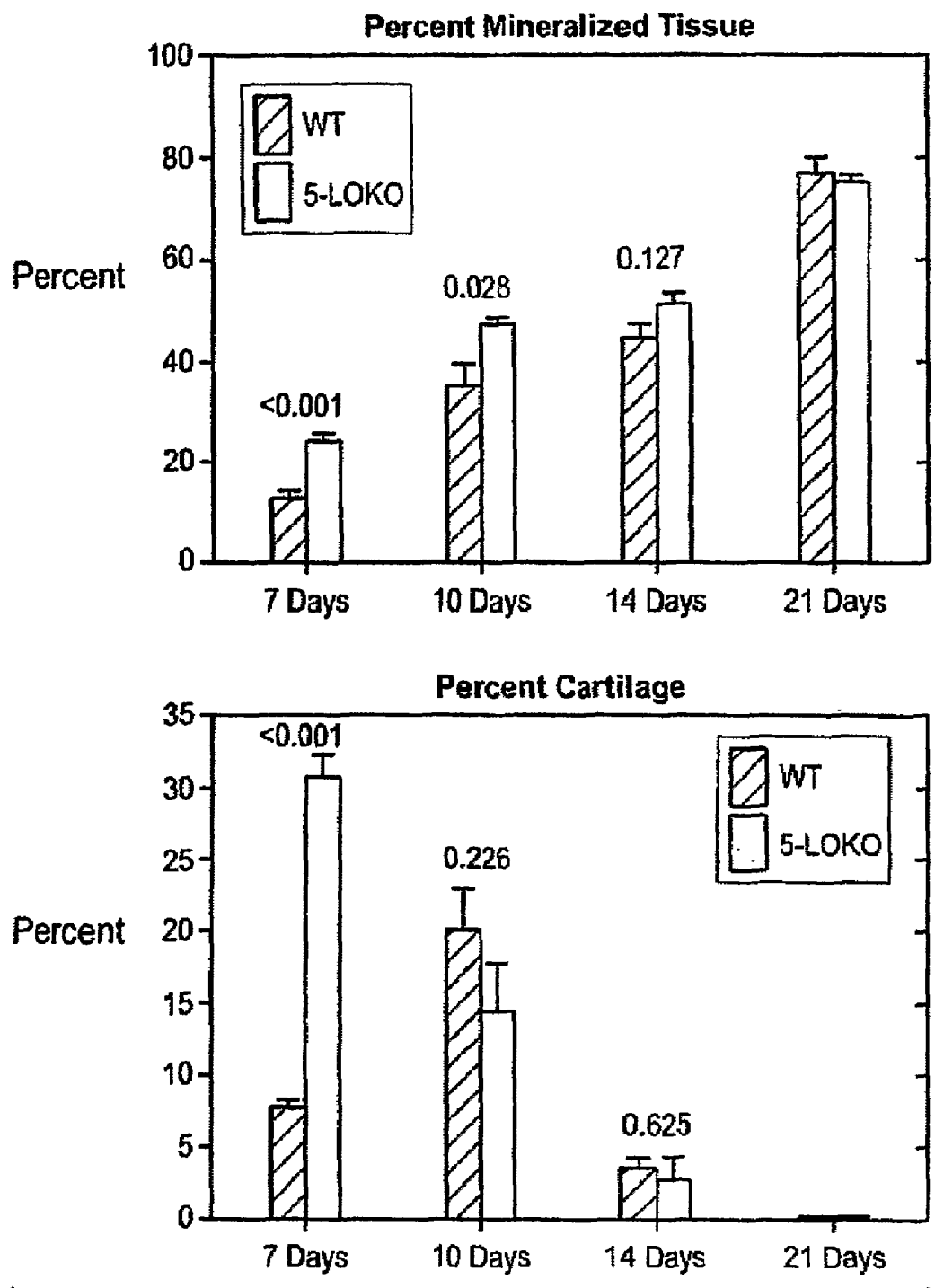
FIG. 5 illustrates histomorphometric data of fracture healing from wild-type (WT) and 5-LO knockout mice (5-LOKO or 5-LO-/-) at 7, 10, 14, and 21 days after fracture. The left panel shows the percent of fracture callus area that is newly formed bone (mineralized tissue) and the right panel shows the percent of fracture callus area that is cartilage.

Histological examination of calcified samples supported the radiographic data. Plastic embedded, calcified sections of normal and 5-LO-/- mouse fractures stained with Stevenel's blue and van Gieson's picrofuchsin show that after just 2 weeks of healing the fracture was bridged with calcified tissue in the 5-LO-/- mice while the normal mouse (C57BL/6) still had a cartilaginous soft callus. Histomorphometric measurements of fracture callus cartilage area showed that cartilage area peaked by day 7 post-fracture in 5-LO-/- mice and by day 10 post-fracture in normal mice (FIG. 5 and TABLE 3). Measurement of new bone (calcified tissue) in the fracture callus showed that almost twice as much new bone in the 5-LO-/- after 7 days of healing and significantly more new bone at day 10 as well (FIG. 5 and TABLE 2). These data show that a normal, albeit significantly accelerated, endochondral ossification pathway is used to heal the fracture in the 5-LO-/- mice. Experiments using younger and older 5-LO-/- mice and in different genetic backgrounds gave identical results: loss of 5-LO function results in accelerated bone regeneration.

The data from these experiments show that a 10 day fracture callus in 5-LO-/- mouse is equivalent to a 14 day callus in a normal mouse; that a 14 day 5-LO-/- callus is equivalent to a 21 day normal callus; and that a 1 month 5-LO-/- callus is equivalent to a 3 month normal callus (FIG. 3). Thus, loss of 5-LO function accelerates and/or enhances the regenerative and remodeling phases of fracture healing.

In one aspect of the invention, compounds that inhibit 5-lipoxygenase activity accelerate and/or enhance healing of a bone fracture or prevent bone resorption or promote bone formation provide important benefits to efforts at treating human disease. Compounds that inhibit 5-lipoxygenase activity can be used, e.g., in a method for treating bone fracture due to trauma, or due to osteoporosis or osteoarthritis, in a method for treating Paget's disease, in a method for treating other conditions such as bone transplants and diseases associated with increased bone fracture, and in methods that require bone formation such as spine fusions, other bone and joint ankylosis procedures, bone or limb lengthening, augmentation of bone structure, incorporation of allograft, autograft, or synthetic bone material into bone defects, bone growth into or around prosthetic devices, and other similar procedures.

Several inhibitors of 5-lipoxygenase and their dosing are known which are useful for practicing the methods of the invention. A 5-lipoxygenase inhibitor can be 3-[1-(4-chlorobenzyl)-3-t-butyl-thio-5-isopropylindol-2-yl]-2,2-dimethylpropanoic acid (MK886) or derivatives thereof; 3-(1-(4-chlorobenzyl)-3-(1-butyl-thio)-5-(quinolin-2-yl-methoxy)-indol-2-yl)-2,2-dimethyl propanoic acid) (MK-591) or derivatives thereof; nordihydroguaiaretic acid (NDGA) or derivatives thereof; 2-(12-hydroxydodeca-5,10-diynyl)-3,5,6-trimethyl-1,4-benzoquinone (AA861) or derivatives thereof; or (N-(1-benzo(b)thien-2-ylethyl)-N-hydroxyurea) (Zileuton) or derivatives thereof. Derivatives include, e.g., pharmaceutically acceptable salts, prodrugs, etc. which also are useful as 5-lipoxygenase inhibitors. Derivatives of exemplary compounds are intended to be within the scope of the claimed invention.

Other 5-lipoxygenase inhibitors for use in the invention include masoprocol, tenidap, flobufen, lonapalene, tagorizine, Abbott A-121798, Abbott A-76745, Abbott A-78773, Abbott A-79175, Abbott ABT 761, Dainippon AL-3264, Bayer Bay-x-1005, Biofor BF-389, bunaprolast, Cytomed CMI-392, Takeda CV-6504, enazadrem phosphate, Leo Denmark ETH-615, flezelastine hydrochloride, Merck Frosst L-663536, Merckle ML-3000, 3M Pharmaceuticals R-840, rilopirox, Schering Plough SCH-40120, tepoxalin, linazolast (TMK-688), Zeneca ZD-2138, Bristol-Myers Squibb BU-4601A, carbazomycin C, lagunamycin, Wellcome BW-70C, Ciba-Geigy CGS-26529, Warner-Lambert CI 1004, Warner-Lambert PD-136005, Warner-Lambert PD-145246, Elsai E-3040, Fujirebio F-1322, Fujisawa FR-110302, Merck Frosst L-699333, Merck Frosst L-739010, Lilly LY-269415, Lilly LY-178002, Hoechst Roussel P-8892, SmithKline Beecham SB-202235, American Home Products WAY-121520, American Home Products WAY-125007, Zeneca ZD-7717, Zeneca ZM-216800, Zeneca ZM-230487, 1,2-dihydro-n-(2-thiazolyl)-1-oxopyrrolo (3,2,1-kl)phenotlliazine-1-carboxamide, Abbott A-65260, Abbott A-69412, Abbott-63162, American Home Products AHR-5333, Bayer Bay-q-1531, Boehringer Ingelheim BI-L-357, Boehringer Ingelheim BI-L-93BS, Boehringer Ingelheim BIL 226XX, Bristol-Myers Squibb BMY-30094, carbazomycin B, Wellcome BW-B218C, Chauvin CBS-1114, Ciba-Geigy CGS-21595, Ciba-Geigy CGS-22745, Ciba-Geigy CGS-23885, Ciba-Geigy CGS 24891, Ciba-Geigy CGS-8515, Chiesi CHF-1909, Warner-Lambert CI-986, Warner-Lambert CI-987, cirsiliol, docebenone, Eisai E-5110, Eisai E-6080, enofelast, epocarbazolin-A, eprovafen, evandamine, Fisons FPL 62064, Zeneca ICI-211965, Zeneca ICI-216800, Kyowa Haliko KF-8940, Merck & Co L-651392, Merck & Co L-651896, Merck & Co L-652343, Merck & Co L-656224, Merck & Co L-670630, Merck & Co L-674636, Lilly LY-233569, Merck & Co MK-591, Merck & Co L-655240, nitrosoxacin-A, Ono ONO-5349, Ono ONO-LP-219, Ono ONO-LP-269, Warner-Lambert PD-127443, Purdue Frederick PF-5901, Rhone-Poulenc Rorer Rev-5367, Rhone-Poulenc Rorer RG-5901-A, Rhone-Poulenc Rorer RG-6866, Roussel-Uclaf RU-46057, Searle SC-41661A, Searle SC-45662, Sandoz SDZ-210-610, SmithKline Beecham SK&F-104351, SmithKline Beecham SK&F-104493, SmithKline Beecham SK&F-105809, Synthelabo SL-81-0433, Teijin TEI-8005, Terumo TMK-777, Terumo TMK-781, Terumo TMK-789, Terumo TMK-919, Terumo TMK-992, Teikoku Hormone TZI-41127, American Home Products WAY-120739, American Home Products WY-47288, American Home Products WY-48252, American Home Products WY-50295, Yoshitomi Y-19432, 4-{3-[4-(2-methyl-1H-imidazol-1-yl)phenylthio]}phenyl-3,4,5,6-tetrahydro-2H-pyran-4-carboxamide, esculetin, phenidone and its derivatives, BI-L-239, 5,8,11-eicosatriynoic acid (ETI), 5,8,11,14-eicosatetraynoic acid (ETYA), cinnamyl-3,4-dihydroxy-alpha-cyanocinnamate, curcumin, esculeitin, gossypol, caffeic acid, baicalein, 7,7-dimethyleicosadrenoic acid (DEDA), Ly311727, bromoenol lactone, methyl arachidonyl fluorophosphonate, methyl y-linolenyl fluorophosphonate, oleyoxyethyl phosphorylcholine, AACOCF3, n-(p-amylcinnamoyl) anthranilic acid, mepacrine, quinacrine, atabrine, parabromophenacylbromide, aristolochic acid, corticosteroids, Glaxo SmithKline 480848, Glaxo SmithKline 659032, Glaxo SmithKline 677116, BMS-181162, MJ33, and Millennium Pharmaceuticals MLN977.

More preferred 5-lipoxygenase inhibitors include masoprocol, tenidap, zileuton, flobufen, lonapalene, tagorizine, Abbott A-121798, Abbott A-76745, Abbott A-78773, [(R)(+) N'-[[5-(4-fluorophenoxy)fuwan-2-yl]-1-methyl-2-propynyl]-N-hydroxyurea (Abbott A-79175),] Abbott A-79175, Abbott ABT 761, Dainippon AL-3264, Bayer Bay-x-1005, Biofor BF-389, bunaprolast, Cytomed CMI-392, Takeda CV-6504, Ciba-Geigy CGS-26529, enazadrem phosphate, Leo Denmark ETH-615, flezelastine hydrochloride, Merck Frosst L 663536, Merck Frosst L 699333, Merckle ML-3000, 3M Pharmaceuticals R-840, rilopirox, Schering Plough SCH 40120, tepoxalin, linazolast (TMK-688), Zeneca ZD-7717, Zeneca ZM-216800, Zeneca ZM-230487, Zeneca ZD-2138; and NDGA (nondihydroguaiaretic acid).

Even more preferred 5-lipoxygenase inhibitors include tenidap, zileuton, flobufen, lonapalene, tagorizine, AA-861, Abbott A-121798, Abbott A-76745, Abbott A-78773, Abbott A-79175, Abbott ABT 761, Ciba-Geigy CGS-26529, Biofor BF-389, Cytomed CMI-392, Leo Denmark ETH-615, lonapalene, Merck Frosst L 699333, Merckle ML-3000, 3M Pharmaceuticals R-840, linazolast (TMK-688), Zeneca ZD-7717, Zeneca ZM-216800, Zeneca ZM-230487, Zeneca ZD-2138, and NDGA (nondihydroguaiaretic acid).

In another aspect, the invention comprises a 5-LO inhibitor and a COX inhibitor and its use. Preferably, the COX inhibitor is a selective COX-1 inhibitor, i.e., that it inhibits the activity of COX-1 more than it inhibits the activity of COX-2. The use of a 5-LO inhibitor and a COX inhibitor is intended to embrace administration of each inhibitor in a sequential manner in a regimen that will provide beneficial effects of the drug combination, the co-administration of the inhibitors in a substantially simultaneous manner, such as in a single capsule having a fixed ratio of these active agents, or in multiple, separate capsules for each agent, as well as a single compound that inhibits both enzymes.

The COX inhibitor can be selected from the group consisting of celecoxib; rofecoxib; meloxicam; piroxicam; valdecoxib, parecoxib, etoricoxib, CS-502, JTE-522; L-745,337; FR122047; NS398; from non-selective NSAIDs that would include aspirin, ibuprofen, indomethacin CAY10404, diclofenac, ketoprofen, naproxen, ketorolac, phenylbutazone, tolfenainic acid, sulindac, and others, or from steroids or corticosteroids. Compounds which selectively inhibit cyclooxygenase-2 have been described in U.S. Pat. Nos. 5,380,738, 5,344,991, 5,393,790, 5,466,823, 5,434,178, 5,474,995, 5,510,368 and WO documents WO96/06840, WO96/03388, WO96/03387, WO95/15316, WO94/15932, WO94/27980, WO95/00501, WO94/13635, WO94/20480, and WO94/26731, and are otherwise known to those of skill in the art.

Selective COX-1 inhibitors are known in the art. The following is a list of preferred COX-1 selective NSAIDs: SC-560 [Smith et al., Proceedings of the National Academy of Sciences of the United States of America 95:13313-8 (1998)], FR122047 [Dohi et al., European Journal of Pharmacology 243:179-84 (1993)], Valeroyl salicylate, Aspirin. Aspirin is an irreversible cyclooxygenase inhibitor that is rapidly inactivated in vivo. While aspirin can inhibit COX-1 and COX-2, prior treatment with aspirin can inactivate all pre-existing COX-1 before or during expression of COX-2. Thus any new COX-2 that is expressed is active but all "older" COX-1 or COX-2 is inactivated.

The following is a list of NSAIDs that preferentially inhibit COX-1 versus COX-2: Dexketoprofene, Keterolac, Flurbiprofen, Suprofen. See also [Warner et al., Proceedings of the National Academy of Sciences of the United States of America 96:7563-8 (1999)].

In another embodiment, the invention comprises a 5-LO inhibitor and a COX-2 activator and its use. COX-2 activators also are known in the art. See [Tanabe and Tohnai, Prostaglandins & other Lipid Mediators 68-69:95-114 (20020] for review article concerning regulation of COX-2 gene expression and as a reference for those compounds or treatments listed below without a reference. Preferred COX-2 activators include ultrasound therapy [Sena et al., Ultrasound in Medicine & Biology 31:703-8 (2005)], pulsed electromagnetic fields (PEMF) [Lohmann et al., Journal of Orthopaedic Research 21:326-34 (2003)], BMP2 [Chikazu et al., Journal of Bone and Mineral Research 17:1430-40 (2002)], PDGF, FGF, and PTH and its analogs (PTHrP and teraparatide) [Maciel et al., Journal of Rheumatology 24:2429-35 (1997)]. Other COX-2 activators include Prostaglandins and prostaglandin receptor agonists [Rosch et al., Biochemical and Biophysical Research Communications 338:1171-8 (20050], PDGF (platelet derived growth factor), IL-1 alpha (interleukin 1 alpha), IL-1beta, TNF-alpha (tumor necrosis factor alpha), FGF (fibroblast growth factor), TGF-beta (transforming growth factor beta), TGF-alpha, EGF (epidermal growth factor), TPA (tetradecanoyl phorbol acetate), In addition, the invention comprises a combination comprising a therapeutically-effective amount of a 5-lipoxygenase inhibitor and a cyclooxygenase-2 inhibitor, such as, e.g., licofetone, Dupont Dup 697, Taisho NS-398, meloxicam, flosulide, Glaxo SmithKline 406381, Glaxo SmithKline 644784, or tepoxalin.

The modulation of bone metabolism by the methods of the invention can be determined by examination of bone strength and mass after administration compared to a control subject. Such examination can be performed in situ by using imaging techniques (e.g., X-ray, nuclear magnetic resonance imaging, X-ray tomography, ultrasound, and sound conduction) or stress testing, or ex vivo by standard histological, radiographic, mechanical, or biochemical methods. Modulation of bone density and/or bone mass can be assessed by changes in one or more parameters such as bone mineral density, bone strength, trabecular number, bone size, and bone tissue connectivity. Several methods for determining bone mineral density (BMD) are known in the art. For example, BMD measurements may be done using, e.g., dual energy xray absorptiometry or quantitative computed tomography, and the like. Similarly, increased bone formation can be determined using methods well known in the art. For example, dynamic measurements of bone formation rate (BFR) can be performed on tetracycline labeled cancellous bone from the lumbar spine and distal femur metaphysis using quantitative digitized morphometry (Ling et al., *Endocrinology* 140: 5780-5788 (1999)). Alternatively, bone formation markers, such as alkaline phosphatase activity, serum collagen peptide levels, or serum osteocalcin levels can be assessed to indirectly determine whether increased bone formation has occurred (Looker et al., *Osteoporosis International* 11: 467-480 (2000)). Compounds that modulate an arachidonic acid metabolic or signaling pathway can be tested for their ability to accelerate or enhance fracture healing and/or bone formation, promote bone formation, and prevent bone loss. This can be tested in a variety of animal models well known to one skilled in the art such as animal fracture models, animal osteotomy models, animal skull trephine defect models, animal bone defect models, various animals segmental defect models and bone lengthening models, ovariectomy induced bone loss models, and the like. The utility of these animal models is well established and is supported by a wide range of different observations. For example, BMP2 studies in animals including rats demonstrated that BMP2 stimulates osteogenesis and BMP2 is now used clinically in humans for bone repair applications (tradename INFUSE). There are hundreds of papers about this in animals and tens of papers about humans; NSAIDs inhibit fracture repair in rats [Simon et al., Cyclooxygenase 2 function is essential for bone fracture healing. Journal of Bone and Mineral Research 17:963-76 (2002)] and NSAID use has been correlated to poor fracture healing in humans [Burd et al., Journal of Bone and Joint Surgery (British) 85B:700-5 (2003)]; studies cited in Rubin et al. (2001), JBJS 83(2):259-270 indicating that ultrasound treatment accelerates fracture repair in rats (Azuma ref.) and in humans. FDA guidelines for osteoporosis therapies indicate that preclinical studies require use of 2 species and that one must be an ovariectomized rat model.

Modulation of bone metabolism by the methods of the invention can be determined in vitro by examining the proliferation, survival, and differentiation of osteoblasts and/or chondrocytes following treatment that alters arachidonic acid metabolism as compared to mock treated cells. Treatment of cells or organ explants such as newborn rodent calvaria or phalanges can be with compounds that inhibit 5-lipoxygenase activity, alter cyclooxygenase activity, affect leukotriene or prostaglandin receptor function, and the like as set forth in this application. Additional treatment methods can include use of antisense nucleic acids, interfering RNAs, other nucleic acid or proteins, and the like. Osteoblast or chondrocyte proliferation and survival can be measured by a number of techniques well known to one skilled in the arts such as cell counting, incorporation of radiolabeled thymidine or bromodeoxyuridine into replicating DNA, trypan blue exclusion, and terminal deoxynucleotidyl transferase end labeling of DNA within cells undergoing apoptosis. Differentiation of osteoblasts and/or chondrocytes can be measured by a number of techniques well known to one skilled in the arts and would include formation of mineralized nodules stained by the method of von Kossa or with alizarin red to ascertain osteoblast or chondrocyte culture mineralization, alcian blue staining of chondrocytes to measure elaboration of proteoglycan matrix, gene expression analyses to measure markers of osteoblast and chondrocyte differentiation such as Type I, Type II, and Type X collagen, osteocalcin, and aggrecan using protein or nucleic acid based assay methods, measurement of alkaline phosphatase activity, and measurement of RANKL, OPG, VEGF, bone morphogenetic protein, and other growth factors by quantitative methods such as enzyme-linked immuno assays (EIA).

5-Lipoxygenase-activating Protein (FLAP)

FLAP is an 18-kD membrane-bound polypeptide which specifically binds arachidonic acid and activates 5-LO by acting as an arachidonic acid transfer protein. The FLAP gene spans greater than 31 kb and consists of five small exons and four large exons (GenBank 182657, Genbank M60470 for exon 1, Genbank M63259 for exon 2, Genbank M63260 for exon 3, Genbank M63261 for exon 4, and Genbank M6322 for exon 5).

The nuclear envelope is the intracellular site at which 5-LO and FLAP act to metabolize arachidonic acid, and ionophore activation of neutrophils and monocytes results in the translocation of 5-LO from a nonsedimentable location to the nuclear envelope. Inhibitors of FLAP function prevent translocation of 5-LO from cytosol to the membrane and inhibit 5-LO activation. Thus, FLAP inhibitors are anti-inflammatory drug candidates.

Leukotriene synthesis is reduced by drugs that inhibit FLAP (MK866) or in mice lacking FLAP. Thus, in one aspect of the invention, FLAP inhibitors such as BAYx 1005, MK-886, and MK-0591, are used in methods that modulate an arachidonic acid metabolic or signaling pathway thereby accelerating and/or enhancing fracture healing and bone formation.

Antisense Treatment

The term "antisense nucleic acid" is intended to refer to an oligonucleotide complementary to the base sequences of 5-LO or FLAP-encoding DNA and RNA or those that encode other proteins in an arachidonic acid metabolic or signaling pathway. Antisense oligonucleotides can be modified or unmodified RNA, DNA, or mixed polymer oligonucleotides, and, when introduced into a target cell, specifically bind to their target nucleic acid and interfere with transcription, RNA processing, transport and/or translation. Targeting doublestranded (ds) DNA with oligonucleotide leads to triple-helix formation; targeting RNA will lead to double-helix formation.

Antisense constructs can be designed to bind to the promoter and other control regions, exons, introns or even exon-intron boundaries of a gene. Antisense RNA constructs, or DNA encoding such antisense RNAs, can be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules, where guanine pairs with cytosine (G:C) and adenine pairs with either thymine (A:T) in the case of DNA, or adenine pairs with uracil (A:U) in the case of RNA.

While all or part of the gene sequence may be employed in the context of antisense construction, preferably any sequence 17 bases long can be used to specify a unique target sequence. Although shorter oligomers are easier to make and increase in vivo accessibility, numerous other factors are involved in determining the specificity of hybridization. The antisense oligonucleotide is selected such that the binding affinity and sequence specificity to its complementary target is sufficient for use as therapeutic agents. Thus, oligonucleotides of 8, 9, 10, 11, 12, 13, 14, 15, 16, 17, 18, 19, 20, 21, 22 or more base pairs can be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

Interfering RNA

Interfering RNA (RNAi) fragments, particularly double-stranded (ds) RNAi, can be used to modulate an arachidonic acid metabolism or signaling pathway. Small interfering RNA (siRNA) are typically 19-25 nucleotide-long RNA molecules that interfere with the expression of genes. Methods relating to the use of RNAi to silence genes in *C. elegans, Drosophila*, plants, and humans are known in the art (Fire et al., Nature 391: 806-811 (1998); Sharp, P. A. RNA interference 2001. Genes Dev. 15: 485-490 (2001); Tuschl, T. Chem. Biochem, 2: 239-245 (2001); WO0129058; and WO9932619).

The nucleotide sequence employed RNAi comprises sequences that are at least about 15 to 50 basepairs. The sequence can be a duplex, optionally with overhangs at the 5'-end and/or the 3'-end, where one strand of the duplex comprises a nucleic acid sequence of at least 15 contiguous bases having a nucleic acid sequence of a nucleic acid molecule within an arachidonic acid metabolic or signaling pathway. The length of each strand can be longer where desired, such as 19, 20, 21, 22, 23, 24, 25, or 30 nucleotides or up to the full length of any of those described herein. The single-stranded overhang can be, for example, 1, 2, 3, 4, 5, or 10 nucleotides long, and can be present at the 3'-end, the 5' end, or both the 3'-end and the 5'-end. Such fragments can be readily prepared by directly synthesizing the fragment by chemical synthesis, by application of nucleic acid amplification technology, or by introducing selected sequences into recombinant vectors for recombinant production.

In particular, the nucleotide sequences or RNAi can be oligonucleotides complementary to the base sequences of 5-LO or FLAP-encoding DNA and RNA or to the base sequences encoding other proteins in an arachidonic acid metabolism or signaling pathway. The oligonucleotides can be modified or unmodified RNA, DNA, or mixed polymer oligonucleotides, and, when introduced into a target cell, specifically bind to their target nucleic acid and interfere with transcription, RNA processing, transport and/or translation.

Other Agents

In another aspect of the invention, an additional agent or drug may be administered to the subject. The additional agent can contain one or more active agents that effectively regulate calcium homeostatis, modulate chondrogenesis, modulate osteogenesis, modulate bone remodeling, regulate pain, regulate inflammation, or have antibiotic activity. The additional active agent can be, but is not limited to, an estrogen, an IGF, insulin, bone morphogenetic proteins and other growth factors, osteoprotegrin (OPG), a calcitonin, a bisphosphonate, vitamin $D_3$ or an analogue thereof, a statin, an adrogen, a fluoride salt, a parathyroid hormone or an analogue thereof, agents that enhance angiogenesis such as vascular endothelial growth factor (VEGF), agents that alter regulation of transcription of naturally occurring hormone regulators involved in bone metabolism, a vitamin, a mineral supplement, a nutritional supplement, and combinations thereof. The additional agent also may be an antibiotic such as gentamycin, ciprofloxacin, vancomycin, and/or others. This additional active agent can be administered to the subject prior to, concurrently with or subsequently to administration of the 5-lipoxygenase inhibitor of this invention. Anti-inflammatory drugs, including but not limited to nonsteroidal anti-inflammatory drugs and corticosteroids, p38 kinase inhibitors, and antiviral drugs, including but not limited to ribivirin, vidarabine, acyclovir and ganciclovir, may also be combined in compositions of the invention. Antibiotic compounds including but not limited to gentamicin, teicoplanin, tobramycin, and vancomycin, may also be combined in the composition of the invention.

III. Pharmaceutical Formulations and Modes of Administration

The methods described herein use pharmaceutical compositions comprising the molecules described above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sufobutyl ether cyclodextrins) etc. Suitable excipients for non-liquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences,* 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration, in a form suitable for administration by inhalation or insufflation, or in a form suitable for administration at the bone formation site. The preferred manner of administration is oral or intravenous using a convenient daily dosage regimen which can be adjusted according to the degree of affliction.

Formulations for delivery at the bone formation site include adsorption onto or encapsulation within polylactide and/or polygalactide polymers, palmitic acid, alginate, plaster, calcium sulfate, calcium phosphate, mixtures of calcium sulfate and calcium phosphate, hydroxyapatite, collagen or other extracellular matrix material, bone wax (such as that from CP Medical, Inc., Ethicon, Inc., Unites States Surgical Corp., or Ceremed), Orthocon Bone Putty (a mixture of calcium stearate, vitamin E acetate, and alkylene oxide copolymer) or other materials or compounds that can be used for this purpose. Delivery can be accomplished by direct placement at the bone formation site or by deposition of the active compound of the invention with or without a carrier onto the surface of prosthetic or surgically implanted devices.

A pharmaceutically or therapeutically effective amount of the composition is delivered to the subject. The precise effective amount varies from subject to subject and depends upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount will be in the range of about 0.05 mg/kg to about 40 mg/kg body weight, more preferably about 0.5 mg/kg to about 20 mg/kg, in at least one dose. In larger mammals the indicated daily dosage can be from about 1 mg to 4,800 mg, one or more times per day, more preferably in the range of about 10 mg to 1,200 mg. The subject may be administered as many doses as is required to reduce and/or alleviate the signs, symptoms, or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease. When practicing the methods of the invention starting human doses may need to be estimated from rat dose data. Such estimation methods are well known in the art. See FDA publication "Guidance for Industry: Estimating the Maximum Safe Starting Dose in Initial Clinical Trials for Therapeutics in Adult Healthy Volunteers" published July 2005 (Federal Register Document 5-14456) and available online at www.fda.gov/Cder/guidance/5541fnl.pdf. In general, the rat dose expressed as mg/kg should be divided by 6.2 to obtain an equivalent human dose.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

IV. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

5-LO Knock Out Mice

Knock out mice lacking 5-lipoxygenase (Alox5−/− or 5-LO−/−) were purchased from Jackson Laboratory, Bar Harbor, Me. An impending femur fracture was stabilized with an intramedullary wire that was inserted retrograde into the femoral canal. A three-point bending device was used to male the fracture. Femur fracture healing was measured or assessed by histomorphometry, radiography, and torsional mechanic testing. The 5-LO−/− mice demonstrated statistically significant, quantitative acceleration and enhancement of fracture healing as compared to wild-type mice of identical genetic background and age (C57BL/6). Closed mid-diaphyseal fractures were made in 10-12 week old female mice. Fracture healing was assessed by x-rays (FIG. 3) and quantitatively assessed by torsional mechanical testing 4 and 12 weeks after fracture (FIG. 4 and TABLE 2). After 4 or 12 weeks of healing, the fractured femurs from 5LO−/− and wild type (WT) mice were excised and mechanically tested to failure in torsion using an MTS servohydraulic test machine and Interface 20 Nm torque load cell. Fractured femur dimensions were measured before and after testing. Peak torque, rigidity, maximum shear stress, and shear modulus were calculated from callus dimensions and the torque to angular displacement curves. All mechanical parameters were 50-120% higher after 4 weeks of healing in the 5-LO−/− as compared to the WT mice. Histomorphometric analysis of time-staged fracture specimens from normal and 5-LO−/− mice showed that cartilage area peaked early and to a greater extent in the 5-LO−/− mice (FIG. 5 and TABLE 3). Further, significantly more new bone (mineralized tissue) was present in the 5-LO−/− fracture callus at 7 and 10 days after fracture. The data demonstrate that fracture healing is accelerated and enhanced in the 5LO-KO mice.

TABLE 2

Summary of fractured femur torsional mechanical testing data from 5-LO—/— and wild-type mice of identical genetic background and age at time of fracture (Fx).

| | | | Mean Percentages (Fracture/Contralateral) ± SD | | | |
|---|---|---|---|---|---|---|
| Strain | Sample Size | Days Post-Fx | Peak Torque | Rigidity | Max. Shear Stress | Shear Modulus |
| C57BL/6 | 9 | 28 | 85.3 ± 16.7 | 61.9 ± 31.3 | 18.2 ± 5.4 | 7.8 ± 4.4 |
| C57BL/6 | 6 | 84 | 77.8 ± 20.1 | 110.6 ± 19.1 | 26.2 ± 12.8 | 25.9 ± 13.4 |
| Lox5—/— | 8 | 28 | 128.5 ± 30.3 | 109.9 ± 37.4 | 31.8 ± 9.0 | 17.4 ± 11.1 |
| Lox5—/— | 8 | 84 | 131.4 ± 26.0 | 95.8 ± 37.8 | 49.8 ± 16.9 | 23.2 ± 13.2 |

TABLE 3

Summary of fracture callus histomorphometric analysis from 5-LO—/— and wild-type mice of identical genetic background and age at time of fracture.

| | Percent Cartilage (mean ± S.D.) | | | Percent Mineralized Tissue (mean ± S.D.) | | |
|---|---|---|---|---|---|---|
| Time Point | Wild-Type | 5-LO—/— | P value | Wild-Type | 5-LO—/— | P value |
| 7 days | 7.84 ± 1.31 | 30.84 ± 3.46 | <0.001 | 12.89 ± 3.76 | 24.56 ± 3.33 | <0.001 |
| 10 days | 20.16 ± 6.13 | 14.46 ± 7.53 | 0.226 | 35.49 ± 9.67 | 47.57 ± 2.86 | 0.028 |
| 14 days | 3.63 ± 1.37 | 2.73 ± 3.71 | 0.625 | 44.66 ± 7.14 | 51.46 ± 5.38 | 0.127 |
| 21 days | 0 ± 0 | 0 ± 0 | 1.000 | 77.26 ± 6.26 | 75.72 ± 2.55 | 0.624 |

The serial x-rays (FIG. 3) show that fracture healing is accelerated in the 5LO–/– mice as compared to wild type mice (C57BL/6). More specifically, the 10 day old fracture from the 5LO–/– mouse appears to be at similar stage as the 14 day old fracture from the wild type mouse, the 14 day 5LO–/– fracture is similar to the 21 day wild type fracture, and the 1 month 5LO–/– fracture is similar to a 3 month old wild type fracture. The mechanical testing data show quantitatively that the structural and material properties of the 5-LO–/– fracture callus were statistically significantly better than the controls after 4 weeks of healing with a 50% increase in peak torque, a 75% increase in rigidity, a 75% increase in maximum shear stress, and over a 100% increase in shear modulus. Further, the 4 week mechanical testing parameters from the 5LO–/– mice were similar to those from the 12 week wild type mice, supporting the x-ray data of FIG. 3 and demonstrating that fracture healing was accelerated and enhanced in the 5LO–/– mice. After 12 week of healing, the rigidity and shear modulus of the wild-type fracture callus had caught-up with the 5-LO–/– fracture callus. Histomorphometric measurements of time-staged fracture callus specimens from the 5-LO–/– and WT mice support the mechanical and radiographic observations (FIG. 5 and TABLE 2). Callus cartilage area peaked by day 7 post-fracture in the 5-LO–/– mice but not until day 10 in the WT mice. There was almost 4-times more cartilage present in the 5-LO–/– callus at day 7 as compared to that from the WT mice. Concurrently, more new bone formation also occurred in the 5-LO–/– mice with almost twice as much new bone (mineralized tissue) present at day 7 and 30% more new bone at day 10 as compared to the WT mice. The data is thus consistent with fracture healing occurring faster and producing more mechanically sound fracture callus with enhanced structural and material properties in the 5-LO–/– mice than in normal mice.

EXAMPLE 2

COX-2 Knockout Mice

Fracture healing was assayed in mice with a targeted deletion of the COX-2 gene. Closed, mid-diaphyseal femur fractures were made in the right hindlimb of COX-2 knockout, COX-1 knockout, and wild type mice (not shown). Fracture healing was assessed by x-rays and histology (FIG. 6), and by mechanical testing (not shown). The data show that fracture healing was dramatically impaired in the COX-2 knockout mice, but not the COX-1 knockout or wild type mice. X-rays after 14 days of healing show a large mineralized fracture callus in the COX-1 knockout mouse (FIG. 6) with little or no evident mineralized callus in the COX-2 knockout mouse. Histological examination confirmed the x-ray findings in that the COX-2 knockout callus had a significant amount of cartilage but no new bone was evident. Torsional mechanical testing data shows that fracture callus structural and material properties are statistically significantly worse than COX-1 knockout or wild type mice. When combined with the experimental results of example 1, example 3, and example 4 this demonstrates how arachidonic acid metabolic or signaling can be manipulated according to the methods of the invention to affect bone formation.

EXAMPLE 3

Treatment of Rats with a 5-Lipoxygenase Inhibitor

Sprague-Dawley rats (3 months old) underwent a standard closed femur fracture procedure as described in the art (Simon et al. Journal of Bone and Mineral Research, 17(6): 963-976 (2002); Bonnarens and Einhorn, *Production of a standard closed fracture in laboratory animal bone*. Journal of Orthopaedic Research, 2: 97-101 (1984)). The impending fracture was stabilized with an intramedullary stainless steel pin. Beginning 4 hours after fracture the rats were treated with 30 mg/kg of NDGA (nordihydrogaiaretic acid) in 1% methylcellulose (5-lipoxygenase inhibitor treatment group) or with carrier only (1% methylcellulose). The day after surgery and continuing until day 14 post-fracture, experimental rats were treated with 2 doses of NDGA (30 mg/kg), the first dose between 8-10 AM and then again with another NDGA dose 8-10 hours later. Control rats were treated similarly but with carrier only (1% methylcellulose). Three weeks after fracture, the rats were sacrificed, the fractured femurs were harvested, and high resolution radiographs were made of the fractured femurs using a Packard Faxitron and Kodak MinR2000 mammography film. Two representative radiographs are shown in FIG. 7 for each treatment group: control and 5-lipoxygenase (5-LO) inhibitor treated.

The radiographs show that after 3 weeks the fractured femurs of the 5-LO inhibitor treated rats were bridged with new bone. In contrast, a well-formed, mineralized fracture callus has formed in the control rats but the fracture site had not yet bridged with new bone. In rat C, the fracture is bridged with new bone on the medial (top) and lateral (bottom) sides of the fracture callus. In rat D, the fracture is bridged with new bone on the lateral side (bottom) and shows indications of new bone bridging on the medial side. No new bone bridging is evident in the control rats (rats A and B). The data thus demonstrates that 5-LO inhibitor therapy can accelerate the fracture healing process in young, normal rats.

EXAMPLE 4

Treatment of Rats with 5-Lipoxygenase Inhibitors

Figure 8D:
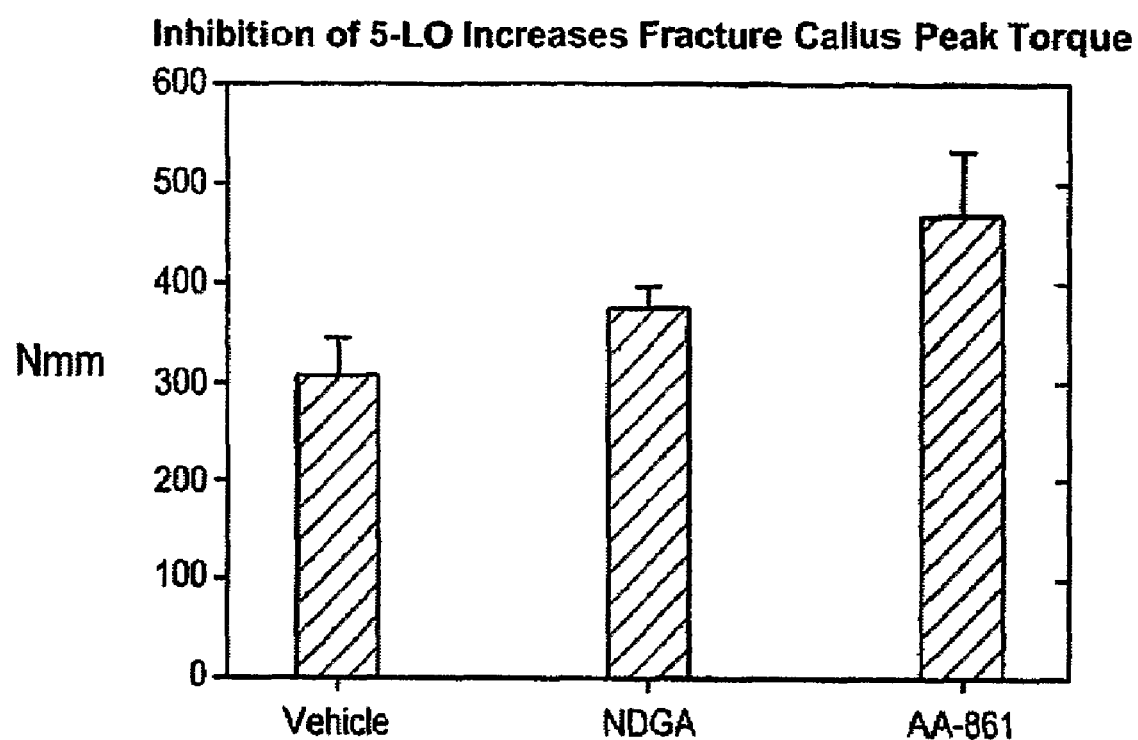
FIG. 8D is a graph showing inhibition of 5-LO increases fracture callus peak torque.

Sprague-Dawley rats (3 months old) underwent a standard closed femur fracture procedure as described in the art (Simon et al. Journal of Bone and Mineral Research, 17(6): 963-976 (2002); Bonnarens and Einhorn, *Production of a standard closed fracture in laboratory animal bone*. Journal of Orthopaedic Research, 2: 97-101 (1984)). The impending fracture was stabilized with an intramedullary stainless steel pin. Beginning 4 hours after fracture the rats were treated with vehicle (1% methylcellulose) or inhibitors of 5-LO suspended in 1% methylcellulose. Inhibitor A (NDGA) was administered at 30 mg/1 g and Inhibitor B (AA-861) was administered at 5 mg/kg. The day after surgery and continuing until day 21 post-fracture, experimental rats were treated with 2 doses of inhibitor (either A or B), the first dose between 8-10 AM and then again with another dose 8-10 hours later. Control rats were treated similarly but with carrier only (1% methylcellulose). Three weeks after fracture the rats were anesthetized and high resolution radiographs were made of the fractured femurs using a Packard Faxitron and Kodak MinR2000 mammography film (FIGS. 8A, 8B, and 8C). Five weeks after fracture the rats were sacrificed, femurs resected, and assayed for structural mechanical properties by torsional mechanical testing (FIG. 8D).

The radiographs showed that after 3 weeks of healing, the fractures appeared bridged in the 5-LO inhibitor treated rats but not in the vehicle treated rat.

Torsional mechanical testing was used to measure the peak torque sustained by each femur after 5 weeks of healing. The data show that the femurs from the Inhibitor A (NDGA) treated rats and from the Inhibitor B treated rats had 22% and 53% greater peak torque than vehicle treated rats (FIG. 5D). In addition, all of the femurs from the Inhibitor A or B treated rats failed as boney unions while 13% (2 of 15) of the femurs from the vehicle treated rats failed as non-unions with no apparent bone bridging.

These experimental observations demonstrate that 5-LO inhibition therapy can accelerate (faster bone bridging) and enhance (better mechanical properties) fracture healing.

EXAMPLE 5

Ex Vivo Treatment Methods Using Small Molecule Compounds. RNAi, and Antisense Compounds Methods to promote ex vivo osteogenesis are used, e.g., to aid in healing of recalcitrant bone fractures, segmental defects caused by traumatic injuries or pathological resection of bone segments, or for joint arthrodesis. In these instances, precursor bone cells are isolated from a subject or from a suitable donor and are cultured ex vivo using standard methods. The cells are grown in or seeded into an appropriate scaffold that either represents the segment of missing bone or can be molded to fit the missing segment or juxtapose the ends of the bone. The cells are induced to form bone ex vivo using appropriate cell culture conditions or with inductive factors, such as bone morphogenetic protein-2 (BMP-2). Once the cells have begun to elaborate a new bone matrix, the construct can be implanted into the patient to effect osteogenesis and promote healing. This sequence of events is typically referred to as a tissue engineering approach to enhancing osteogenesis.

Inhibition of 5-lipoxygenase (5-LO) can be used to promote ex vivo bone formation for tissue engineering application. This is accomplished by promoting osteogenesis ex vivo with small molecule inhibitors of 5-LO or FLAP alone or in combination with well known inductive agents, such as BMP-2.

A second approach uses RNAi technology to inhibit 5-LO activity and promote ex vivo osteogenesis. This is accomplished by transfecting the cultured precursor skeletal cells with pools of siRNA sequences using commercially available transfection reagents, such as TransIT-TKO or jetSI. Approximately 1 million cells are transfected with a cocktail of 3 siRNAs specific for 5-LO or FLAP using 50-200 pmoles of each siRNA. Alternatively, a pool of siRNAs that target 5-LO and FLAP is used. As a control, cells are transfected similarly with commercially available siRNAs developed to knock-down enhanced green fluorescent protein (EGFP). Knock-down of 5-LO or FLAP is confirmed by western blot analysis and the results quantified to insure a greater than 80% reduction in 5-LO and/or FLAP expression.

The treated precursor skeletal cells are cultured and osteogenesis is assessed as extracellular matrix production of cartilage or bone matrix using measures such as alcian blue or alizarin red binding as appropriate or measures of specific matrix protein. Knock-down of 5-LO or FLAP promotes osteogenesis based upon enhanced calcified matrix deposition measured by alizarin red binding. This indicates that an RNAi or anti-sense approach to inhibiting 5-LO activity is useful for promoting osteogenesis ex vivo for purposes of tissue engineering.

Pools of siRNA pairs for 5-LO can be chosen, e.g., from POOL-A (5'-AAC TGG GCG AGA TCC AGC TGG-3' (SEQ ID NO: 9), 5'-AAG CTC CCG GTG ACC ACG GAG-3' (SEQ ID NO: 10), 5'-AAG GAA GCC ATG GCC CGA TTC-3') (SEQ ID NO: 11), POOL-B (5'-AAT CGA GAA GCG CAA GTA CTG-3' (SEQ ID NO: 12), 5'-AAG GAG TGG ACT TTG TTC TGA-3' (SEQ ID NO: 13), 5'-AAC TTC GGC CAG TAC GAC TGG-3') (SEQ ID NO: 14), or POOL-C (5'-AAG TTG GCC CGA GAT GAC CAA-3' (SEQ ID NO: 15), 5'-AAC ACA TCT GGT GTC TGA GGT-3' (SEQ ID NO: 16), 5'-AAC CAT GCG AGC CCC GCC ACC-3') (SEQ ID NO: 17). Pools of siRNA pairs for FLAP can be chosen, e.g., from POOL-D (5'-AAG CAA ACA TGG ATC AAG AAA-3' (SEQ ID NO: 18), 5'-AAG TTC CTG CTG CGT TTG CTG-3' (SEQ ID NO: 19), 5'-AAT TCA GCT CTT GAG AGC ATT-3') (SEQ ID NO: 20), POOL-E (5'-AAT GGA TTC TTT GCC CAT AAA-3' (SEQ ID NO: 21), 5'-AAG TAC TTT GTC GGT TAC CTA-3' (SEQ ID NO: 22), 5'-AAT CTA TTG GCC ATC TGG GCT-3') (SEQ ID NO: 23), or POOL-F (5'-AAC CAG AAC TGT GTA GAT GCG-3' (SEQ ID NO: 24), 5'-AAG TGA CTT TGA AAA CTA CAT-3' (SEQ ID NO: 25), 5'-AAT GAT GTC ATG TCA GCT CCG-3') (SEQ ID NO: 26). For brevity, only the sense strand of each siRNA pair is shown. It is well known in the art that siRNA pairs are double stranded small RNAs that have a 5'-AA overhang on the sense strand and a 5'-UU overhang on the antisense strand. It also is well known in the art that backbone chemistry modifications can be advantageous for stabilizing or improving the uptake of the siRNA molecules. Pirollo K F et al., (2003), Rait A, Sleer L S, Chang E H, "Antisense therapeutics: from theory to clinical practice," Pharmacol Ther. 99(1): 55-77. Manufacture of oligonucleotides with advantageous backbone chemistry modifications is within the level of ordinary skill, and use of such modified-backbone compounds (as well as non-modified-backbone compounds) is within the scope of the present invention.

One skilled in the art will recognize that in addition to direct transfection of the siRNAs into cells, expression vectors can be developed that express these or similar sequences and the expression vectors delivered to the cells by transfection, viral mediated delivery, or methods for delivering DNA molecules into cells. The expression vectors express the siRNAs leading to sustained inhibition of 5-LO, FLAP, or both and thereby promoting osteogenesis.

One skilled in the art also will recognize that additional strategies to inhibit expression of 5-LO or FLAP can be used to promote the same osteogenic effects in the precursor skeletal cells. Such technologies include use of anti-sense.

Exemplary 5-Lipoxygenase anti-sense sequences include, e.g., 5'-GCA GGT GCT TCT CGC TGC AGC C-3' (SEQ ID NO: 27), 5'-GCC AGT ACT TGC GCT TCT CG-3' (SEQ ID NO: 28), 5'-CCA TCG ATA TTG TTT TTG CC-3' (SEQ ID NO: 29), 5'-GGA GCT TCT CGG GCA GCT CTG TGC-3' (SEQ ID NO: 30), 5'-CCA GGT TCT TAT ACA GCA AGC-3' (SEQ ID NO: 31), 5'-CCA GCA GCT TGA AAA TGG GGT GC-3' (SEQ ID NO: 32), 5'-GCC CCG GGC CTT GAT GGC C-3' (SEQ ID NO: 33), 5'-CCA CGC CCT TGG CAG TCG G-3' (SEQ ID NO: 34), and 5'-GCG GAA TCG GGC CAT GGC TTC C-3' (SEQ ID NO: 35).

Exemplary FLAP anti-sense sequences include, e.g., 5'-GTT CCG GTC CTC TGG AAG CTC C-3' (SEQ ID NO: 36), 5'-CGC AGA CCA GAG CAC AGC G-3' (SEQ ID NO: 37), 5'-GCA AAC GCA GCA GGA AC-3' (SEQ ID NO: 38), 5'-CGT TTC CCA AAT ATG TAG CC-3' (SEQ ID NO: 39), 5'-GTT TTC AAA GTC ACT TCC G-3' (SEQ ID NO: 40), 5'-GGT TAA CTC AAG CTG TGA AGC-3' (SEQ ID NO: 41), 5'-GGA GCT GAC ATG ACA TC-3' (SEQ ID NO: 42), and 5'-GGC CAC GGT CAT GTT CAA GG-3' (SEQ ID NO: 43).

Thus, novel methods for promoting osteogenesis to accelerate or enhance bone fracture healing, treat bone defects, and enhance bone formation are disclosed. Although preferred embodiments of the subject invention have been described in some detail, it is understood that obvious variations can be made without departing from the spirit and the scope of the invention as defined by the appended claims.

I claim:

1. A method for promoting osteogenesis to treat a mammalian subject in need thereof, comprising: administering to said subject a pharmaceutically effective amount of compound that reduces a 5-lipoxygenase activity, wherein said 5-lipoxygenase activity reduction promotes osteogenesis to treat a condition selected from the group consisting of a bone fracture, a bone defect, and a condition treated by inducing bone formation.

2. The method of claim 1, wherein said condition is a bone fracture.

3. The method of claim 2, wherein said bone fracture is a non-osteoporotic fracture, an osteoporotic fracture, a fracture associated with a congenital disease, a fracture associated with an acquired disease, or an osteotomic fracture.

4. The method of claim 3, wherein said bone fracture is a non-osteoporotic fracture.

5. The method of claim 3, wherein said bone fracture is an osteoporotic fracture.

6. The method of claim 3, wherein said bone fracture is an osteotomic fracture.

7. The method of claim 1, wherein said condition is a condition treated by inducing bone formation.

8. The method of claim 7, wherein said condition is a condition treated by a spine fusion, or a joint arthrodesis.

9. The method of claim 1, wherein said condition is a bone defect.

10. The method of claim 1, wherein said administration is in vivo.

11. The method of claim 1, wherein said administration is ex vivo.

12. The method of claim 1, wherein said compound reduces a 5-lipoxygenase activity by inhibiting a five lipoxygenase activating protein (FLAP).

13. The method of claim 1, wherein said compound comprises a small molecule.

14. The method of claim 13, wherein said small molecule is selected from the group consisting of 3-[1-(4-chlorobenzyl)-3-t-butyl-thio-5-isopropylindol-2-yl]-2,2-dimethylpropanoic acid; 3-(1-(4-chlorobenzyl)-3-(1-butyl-thio)-5-(quinolin-2-yl-methoxy)-indol -2-y l)-2,2-dimethyl propanoic acid); nordihydroguaiaretic acid; 2-(12-hydroxydodeca-5,10-diynyl)-3,5,6-trimethyl-1,4-benzoquinone; (N-(1-benzo(b)thien-2-ylethyl)-N-hydroxyurea); masoprocol; tenidap; flobufen; lonapalene; tagorizine; Abbott® A-121798; Abbott® A-76745; Abbott® A-78773; [(R)(+)N'-[[5-(4-fluorophenoxy) furan-2-yl]-1-methyl-2-propynyl]-N-hydroxyurea; Abbott® ABT 761; Dainippon® AL-3264; Bayer® Bay-x-1005; Biofor® BF-389; bunaprolast; Cytomed® CMI-392; Takeda® CV-6504; enazadrem phosphate; Leo Denmark® ETH-615; flezelastine hydrochloride; Merck Frosst® L-663536; Merckle® ML-3000; 3M Pharmaceuticals® R-840; rilopirox; Schering Plough® SCH-40120; tepoxalin; linazolast-; Zeneca® ZD-2138; Bristol-Myers Squibb® BU-4601A; carbazomycin C; lagunamycin; Wellcome® BW-70C; Ciba-Geigy® CGS-26529; Warner-Lambert® CI 1004; Warner-Lambert® PD-136005; Warner-Lambert® PD-145246; Elsai® E-3040; Fujirebio® F-1322; Fujisawa® FR-110302; Merck Frosst® L-699333; Merck Frosst® L-739010; Lilly® LY-269415; Lilly® LY-178002; Hoechst Roussel® P-8892; SmithKline Beecham® SB-202235; American Home Products® WAY-121520; American Home Products® WAY-125007; Zeneca® ZD-7717; Zeneca® ZM-216800; Zeneca® ZM-230487; 1,2-dihydro-n-(2-thiazolyl)-1-oxopyrrolo (3,2,1-kl)phenothiazine-1-carboxamide; Abbott® A-65260; Abbott® A-69412; Abbott® A-63162; American Home Products® AHR-5333; Bayer® Bay-q-1531; Boehringer Ingelheim® BI-L-357; Boehringer Ingelheim® BI-L-93BS; Boehringer Ingelheim® BIL 226XX; Bristol-Myers Squibb® BMY-30094; carbazomycin B; Wellcome® BW-B218C; Chauvin® CBS-1114; Ciba-Geigy® CGS-21595; Ciba-Geigy® CGS-22745; Ciba-Geigy® CGS-23885; Ciba-Geigy® CGS 24891; Ciba-Geigy® CGS-8515; Chiesi® CHF-1909; Warner-Lambert® CI-986; Warner-Lambert® CI 987; cirsiliol; docebenone; Eisai® E-5110; Eisai® E-6080; enofelast; epocarbazolin-A; eprovafen; evandamine; Fisons® FPL 62064; Zeneca® ICI-211965; Zeneca® ICI-216800; Kyowa Hakko® KF-8940; Merck® L-651392; Merck® L-651896; Merck® L-652343; Merck® L-656224; Merck® L-670630; Merck® L-674636; Lilly® LY-233569; Merck® MK-591; Merck® L-655240; nitrosoxacin-A; Ono® ONO-5349; Ono® ONO-LP-219; Ono® ONO-LP-269; Warner-Lambert® PD-127443; Purdue Frederick® PF-5901; Rhone-Poulenc Rorer® Rev-5367; Rhone-Poulenc Rorer® RG-5901-A; Rhone-Poulenc Rorer® RG-6866; Roussel-Uclaf® RU-46057; Searle® SC-41661A; Searle® SC-45662; Sandoz® SDZ-210-610; SmithKline Beecham® SK&F-104351; SmithKline Beecham® SK&F-104493; SmithKline Beecham® SK&F-105809; Synthelabo® SL-81-0433; Teijin® TEI-8005; Terumo® TMK-777; Terumo® TMK-781; Terumo® TMK-789; Terumo® TMK-919; Terumo® TMK-992; Teikoku Hormone® TZI-41127; American Home Products® WAY-120739; American Home Products® WY-47288; American Home Products® WY-48252; American Home Products® WY-50295; Yoshitomi® Y-19432; 4-{3-[4-(2-methyl-1H-imidazol-1-yl)phenylthio]}phenyl-3,4,5,6-tetrahydro-2H-pyran-4-carboxamide; esculetin; phenidone; Boehringer Ingelheim® BI-L-239; 5,8,11-eicosatriynoic acid; 5,8,11,14-eicosatetraynoic acid; cinnamyl-3,4-dihydroxy-alpha-cyanocinnamate; curcumin; gossypol; caffeic acid; baicalein; 7,7-dimethyleicosadrenoic acid; Lilly® LY-311727; bromoenol lactone; methyl arachidonyl fluorophosphonate; methyl y-linolenyl fluorophosphonate; oleyoxyethyl phosphorylcholine; arachidonyl trifluoromethyl ketone; n-(p-amylcinnamoyl) anthranilic acid; mepacrine; quinacrine; atabrine; parabromophenacylbromide; aristolochic acid; cortisone; Glaxo SmithKline® SB-480848; Glaxo SmithKline® SB-659032; Glaxo SmithKline® SB-677116; Bristol-Myers Squibb® BMS-181162; Sterling-Winthrop® MJ33; and Millennium Pharmaceuticals® MLN977.

15. The method of claim 14, wherein said small molecule is selected from the group consisting of masoprocol; tenidap; (N-(1-benzo(b)thien-2-ylethyl)-N-hydroxyurea); flobufen; lonapalene; tagorizine; 2-(12-hydroxydodeca-5,10-diynyl)-3,5,6-trimethyl-1,4-benzoquinone; Abbott® A-121798; Abbott® A-76745; Abbott® A-78773; [(R)(+)N'-[[5-(4-fluorophenoxy)furan-2-yl]-1-methyl-2-propynyl]-N-hydroxyurea; Abbott® ABT 761; Dainippon® AL-3264; Bayer® Bay-x-1005; Biofor® BF-389; bunaprolast; Cytomed® CMI-392; Takeda® CV-6504; Ciba-Geigy® CGS-26529; enazadrem phosphate; Leo Denmark® ETH-615; flezelastine hydrochloride; Merck Frosst® L-663536; Merck Frosst® L-699333; Merckle® ML-3000, 3M Pharmaceuticals® R-840; rilopirox; Schering Plough® SCH-40120; tepoxalin; linazolast; Zeneca® ZD-7717; Zeneca® ZM-216800; Zeneca® ZM-230487; Zeneca® ZD-2138; and nordihydroguaiaretic acid.

16. The method of claim 15, wherein said small molecule is selected from the group consisting of tenidap; (N-(1-benzo (b)thien-2-ylethyl)-N-hydroxyurea); flobufen; lonapalene; tagorizine; 2-(12-hydroxydodeca-5,10-diynyl)-3,5,6-trimethyl -1,4-benzoquinone; Abbott® A-121798; Abbott® A-76745; Abbott® A-78773; [(R)(+)N'-[[5-(4-fluorophenoxy)furan-2-yl]-1-methyl-2-propynyl]-N-hydroxyurea; Abbott® ABT 761; Ciba-Geigy® CGS-26529; Biofor® BF-389; Cytomed® CMI-392; Leo Denmark® ETH-615;, Merck Frosst® L 699333; Merckle® ML-3000; 3M Pharmaceuticals® R-840; linazolast; Zeneca® ZD-7717; Zeneca® ZM-216800; Zeneca® ZM-230487; Zeneca® ZD-2138, and nordihydroguaiaretic acid.

17. The method of claim 11, wherein said compound comprises a nucleic acid comprising a sequence selected from the group consisting of 5'-AAC TGG GCG AGA TCC AGC TGG-3' (SEQ ID NO: 9), 5'-AAG CTC CCG GTG ACC ACG GAG-3' (SEQ ID NO: 10), 5'-AAG GAA GCC ATG GCC CGA TTC-3' (SEQ ID NO: 11), 5'-AAT CGA GAA GCG CAA GTA CTG-3' (SEQ ID NO: 12), 5'-AAG GAG TGG ACT TTG TTC TGA-3' (SEQ ID NO: 13), 5'-AAC TTC GGC CAG TAC GAC TGG-3' (SEQ ID NO: 14), 5'-AAG TTG GCC CGA GAT GAC CAA-3' (SEQ ID NO: 15), 5'-AAC ACA TCT GGT GTC TGA GGT-3' (SEQ ID NO: 16), 5'-AAC CAT GCG AGC CCC GCC ACC-3' (SEQ ID NO: 17), 5'-AAG CAA ACA TGG ATC AAG AAA-3' (SEQ ID NO: 18), 5'-AAG TTC CTG CTG CGT TTG CTG-3' (SEQ ID NO: 19), 5'-AAT TCA GCT CTT GAG AGC ATT-3' (SEQ ID NO: 20), 5'-AAT GGA TTC TTT GCC CAT AAA-3' (SEQ ID NO: 21), 5'-AAG TAC TTT GTC GGT TAC CTA-3' (SEQ ID NO: 22), 5'-AAT CTA TTG GCC ATC TGG GCT-3' (SEQ ID NO: 23), 5'-AAC CAG AAC TGT GTA GAT GCG-3' (SEQ ID NO: 24) 5'-AAG TGA CTT TGA AAA CTA CAT-3' (SEQ ID NO: 25), and 5'-AAT GAT GTC ATG TCA GCT CCG-3' (SEQ ID NO: 26).

18. The method of claim 11, wherein said compound comprises a nucleic acid comprising a sequence selected from the group consisting of 5'-GCA GGT GCT TCT CGC TGC AGC C-3' (SEQ ID NO: 27), 5'-GCC AGT ACT TGC GCT TCT CG-3' (SEQ ID NO: 28), 5'-CCA TCG ATA TTG TTT TTG CC-3' (SEQ ID NO: 29), 5'-GGA GCT TCT CGG GCA GCT CTG TGC-3' (SEQ ID NO: 30), 5'-CCA GGT TCT TAT ACA GCA AGC-3' (SEQ ID NO: 31), 5'-CCA GCA GCT TGA AAA TGG GGT GC-3' (SEQ ID NO: 32), 5'-GCC CCG GGC CTT GAT GGC C-3' (SEQ ID NO: 33), 5'-CCA CGC CCT TGG CAG TCG G-3' (SEQ ID NO: 34), 5'-GCG GAA TCG GGC CAT GGC TTC C-3' (SEQ ID NO: 35), 5'-GTT CCG GTC CTC TGG AAG CTC C-3' (SEQ ID NO: 36), 5'-CGC AGA CCA GAG CAC AGC G-3' (SEQ ID NO: 37), 5'-GCA AAC GCA GCA GGA AC-3' (SEQ ID NO: 38), 5'-CGT TTC CCA AAT ATG TAG CC-3' (SEQ ID NO: 39), 5'-GTT TTC AAA GTC ACT TCC G-3' (SEQ ID NO: 40), 5'-GGT TAA CTC AAG CTG TGA AGC-3' (SEQ ID NO: 41), 5'-GGA GCT GAC ATG ACA TC-3' (SEQ ID NO: 42), and 5'-GGC CAC GGT CAT GTT CAA GG-3' (SEQ ID NO: 43).

19. The method of claim 1, further comprising administering to said subject a pharmaceutically effective amount of a compound that reduces a COX-1 activity.

20. The method of claim 19, wherein said compound is selected from the group consisting of Searle® SC-560, 1-[(4, 5-bis(4-methoxyphenyl)-2-thiazoyl)carbonyl]-4-methylpiperazine hydrochloride valeryl salicylate, aspirin, dexketoprofen, ketorolac, flurbiprofen, and suprofen.

21. The method of claim 1, further comprising administering to said subject a pharmaceutically effective amount of a compound that increases a COX-2 activity.

22. The method of claim 21, wherein said compound is selected from the group consisting of prostaglandin E2; butaprost; sulprostone; Pfizer® CP-536,745-01; Pfizer® CP-043,305-02; Pfizer® CP-044,519-02; Pfizer® CP432; Ono Pharmaceutical® ONO-4819; Pfizer® CP-533,536; prostaglandin $F_{2\alpha}$; bimatoprost; cloprostenol; latanoprost; tafluprost; bone morphogenetic protein-2; platelet derived growth factor; interleukin-1α; interleukin-1β; tumor necrosis factor-alpha; fibroblast growth factor, transforming growth factor-β; epidermal growth factor; parathyroid hormone; parathyroid hormone related peptide; and teriparatide.

23. The method of claim 1, comprising administering to said subject an ultrasound therapy or exposing said subject to a pulsed electromagnetic field in an amount sufficient to increase a COX-2 activity in said subject.

24. The method of claim 16, wherein said 5-LO inhibitor is [(R)(+)N'-[[5-(4-fluorophenoxy) furan-2-yl]-1-methyl-2-propynyl]-N-hydroxyurea.

25. The method of claim 16, wherein said 5-LO inhibitor is Abbott® ABT 761.

* * * * *

SEQUENCE LISTING

<160> NUMBER OF SEQ ID NOS: 43

<210> SEQ ID NO 1
<211> LENGTH: 2568
<212> TYPE: DNA
<213> ORGANISM: Homo sapiens

<400> SEQUENCE: 1

| | | | | | |
|---|---|---|---|---|---|
| gccagggacc | agtggtggga | ggaggctgcg | gcgctagatg | cggacacctg | gaccgccgcg | 60 |
| ccgaggctcc | cggcgctcgc | tgctcccgcg | gcccgcgcca | tgccctccta | cacggtcacc | 120 |
| gtggccactg | gcagccagtg | gttcgccggc | actgacgact | acatctacct | cagcctcgtg | 180 |
| ggctcggcgg | gctgcagcga | gaagcacctg | ctggacaagc | ccttctacaa | cgacttcgag | 240 |
| cgtggcgcgg | tggattcata | cgacgtgact | gtggacgagg | aactgggcga | gatccagctg | 300 |
| gtcagaatcg | agaagcgcaa | gtactggctg | aatgacgact | ggtacctgaa | gtacatcacg | 360 |
| ctgaagacgc | cccacgggga | ctacatcgag | ttccctgct | accgctggat | caccggcgat | 420 |
| gtcgaggttg | tcctgaggga | tggacgcgca | aagttggccc | gagatgacca | aattcacatt | 480 |
| ctcaagcaac | accgacgtaa | agaactggaa | acacggcaaa | acaatatcg | atggatggag | 540 |
| tggaaccctg | gcttcccctt | gagcatcgat | gccaaatgcc | acaaggattt | accccgtgat | 600 |
| atccagtttg | atagtgaaaa | aggagtggac | tttgttctga | attactccaa | agcgatggag | 660 |
| aacctgttca | tcaaccgctt | catgcacatg | ttccagtctt | cttggaatga | cttcgccgac | 720 |
| tttgagaaaa | tctttgtcaa | gatcagcaac | actatttctg | agcgggtcat | gaatcactgg | 780 |
| caggaagacc | tgatgtttgg | ctaccagttc | ctgaatggct | gcaaccctgt | gttgatccgg | 840 |
| cgctgcacag | agctgcccga | gaagctcccg | gtgaccacgg | agatggtaga | gtgcagcctg | 900 |
| gagcggcagc | tcagcttgga | gcaggaggtc | cagcaaggga | acattttcat | cgtggacttt | 960 |
| gagctgctgg | atggcatcga | tgccaacaaa | acagacccct | gcacactcca | gttcctggcc | 1020 |
| gctcccatct | gcttgctgta | taagaacctg | gccaacaaga | ttgtccccat | tgccatccag | 1080 |
| ctcaaccaaa | tcccgggaga | tgagaaccct | attttcctcc | cttcggatgc | aaaatacgac | 1140 |
| tggcttttgg | ccaaaatctg | ggtgcgttcc | agtgacttcc | acgtccacca | gaccatcacc | 1200 |
| caccttctgc | gaacacatct | ggtgtctgag | gttttttggca | ttgcaatgta | ccgccagctg | 1260 |
| cctgctgtgc | accccatttt | caagctgctg | gtggcacacg | tgagattcac | cattgcaatc | 1320 |
| aacaccaagg | cccgtgagca | gctcatctgc | gagtgtggcc | tctttgacaa | ggccaacgcc | 1380 |
| acaggggggcg | gtgggcacgt | gcagatggtg | cagagggcca | tgaaggacct | gacctatgcc | 1440 |
| tccctgtgct | ttcccgaggc | catcaaggcc | cggggcatgg | agagcaaaga | agacatcccc | 1500 |
| tactacttct | accgggacga | cgggctcctg | gtgtgggaag | ccatcaggac | gttcacggcc | 1560 |
| gaggtggtag | acatctacta | cgagggcgac | caggtggtgg | aggaggaccc | ggagctgcag | 1620 |
| gacttcgtga | acgatgtcta | cgtgtacggc | atgcggggcc | gcaagtcctc | aggcttcccc | 1680 |
| aagtcggtca | gagccggga | gcagctgtcg | gagtacctga | ccgtggtgat | cttcaccgcc | 1740 |
| tccgcccagc | acgccgcggt | caacttcggc | cagtacgact | ggtgctcctg | gatccccaat | 1800 |
| gcgcccccaa | ccatgcgagc | cccgccaccg | actgccaagg | gcgtggtgac | cattgagcag | 1860 |
| atcgtggaca | cgctgcccga | ccgcggccgc | tcctgctggg | atctgggtgc | agtgtgggcg | 1920 |
| ctgagccagt | tccaggaaaa | cgagctgttc | ctgggcatgt | acccagaaga | gcattttatc | 1980 |
| gagaagcctg | tgaaggaagc | catggcccga | ttccgcaaga | acctcgaggc | cattgtcagc | 2040 |

-continued

```
gtgattgctg agcgcaacaa gaagaagcag ctgccatatt actacttgtc cccagaccgg    2100
attccgaaca gtgtggccat ctgagcacac tgccagtctc actgtgggaa ggccagctgc    2160
cccagccaga tggactccag cctgcctggc aggctgtctg gccaggcctc ttggcagtca    2220
catctcttcc tccgaggcca gtacctttcc atttattctt tgatcttcag ggaactgcat    2280
agattgatca aagtgtaaac accataggga cccattctac acagagcagg actgcacagc    2340
gtcctgtcca cacccagctc agcatttcca caccaagcag caacagcaaa tcacgaccac    2400
tgatagatgt ctattcttgt tggagacatg ggatgattat tttctgttct atttgtgctt    2460
agtccaattc cttgcacata gtaggtaccc aattcaatta ctattgaatg aattaagaat    2520
tggttgccat aaaataaat cagttcattt aaaaaaaaaa aaaaaaa                    2568
```

<210> SEQ ID NO 2
<211> LENGTH: 674
<212> TYPE: PRT
<213> ORGANISM: Homo sapiens

<400> SEQUENCE: 2

```
Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
            20                  25                  30

Ser Glu Lys His Leu Leu Asp Lys Pro Phe Tyr Asn Asp Phe Glu Arg
        35                  40                  45

Gly Ala Val Asp Ser Tyr Asp Val Thr Val Asp Glu Glu Leu Gly Glu
    50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
            100                 105                 110

Arg Asp Gly Arg Ala Lys Leu Ala Arg Asp Asp Gln Ile His Ile Leu
        115                 120                 125

Lys Gln His Arg Arg Lys Glu Leu Glu Thr Arg Gln Lys Gln Tyr Arg
    130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
            180                 185                 190

Arg Phe Met His Met Phe Gln Ser Ser Trp Asn Asp Phe Ala Asp Phe
        195                 200                 205

Glu Lys Ile Phe Val Lys Ile Ser Asn Thr Ile Ser Glu Arg Val Met
    210                 215                 220

Asn His Trp Gln Glu Asp Leu Met Phe Gly Tyr Gln Phe Leu Asn Gly
225                 230                 235                 240

Cys Asn Pro Val Leu Ile Arg Arg Cys Thr Glu Leu Pro Glu Lys Leu
                245                 250                 255

Pro Val Thr Thr Glu Met Val Glu Cys Ser Leu Glu Arg Gln Leu Ser
            260                 265                 270

Leu Glu Gln Glu Val Gln Gln Gly Asn Ile Phe Ile Val Asp Phe Glu
```

-continued

```
                275                 280                 285
Leu Leu Asp Gly Ile Asp Ala Asn Lys Thr Asp Pro Cys Thr Leu Gln
        290                 295                 300
Phe Leu Ala Ala Pro Ile Cys Leu Leu Tyr Lys Asn Leu Ala Asn Lys
305                 310                 315                 320
Ile Val Pro Ile Ala Ile Gln Leu Asn Gln Ile Pro Gly Asp Glu Asn
                325                 330                 335
Pro Ile Phe Leu Pro Ser Asp Ala Lys Tyr Asp Trp Leu Leu Ala Lys
                340                 345                 350
Ile Trp Val Arg Ser Ser Asp Phe His Val His Gln Thr Ile Thr His
                355                 360                 365
Leu Leu Arg Thr His Leu Val Ser Glu Val Phe Gly Ile Ala Met Tyr
        370                 375                 380
Arg Gln Leu Pro Ala Val His Pro Ile Phe Lys Leu Leu Val Ala His
385                 390                 395                 400
Val Arg Phe Thr Ile Ala Ile Asn Thr Lys Ala Arg Glu Gln Leu Ile
                405                 410                 415
Cys Glu Cys Gly Leu Phe Asp Lys Ala Asn Ala Thr Gly Gly Gly Gly
                420                 425                 430
His Val Gln Met Val Gln Arg Ala Met Lys Asp Leu Thr Tyr Ala Ser
                435                 440                 445
Leu Cys Phe Pro Glu Ala Ile Lys Ala Arg Gly Met Glu Ser Lys Glu
        450                 455                 460
Asp Ile Pro Tyr Tyr Phe Tyr Arg Asp Asp Gly Leu Leu Val Trp Glu
465                 470                 475                 480
Ala Ile Arg Thr Phe Thr Ala Glu Val Val Asp Ile Tyr Tyr Glu Gly
                485                 490                 495
Asp Gln Val Val Glu Glu Asp Pro Glu Leu Gln Asp Phe Val Asn Asp
                500                 505                 510
Val Tyr Val Tyr Gly Met Arg Gly Arg Lys Ser Ser Gly Phe Pro Lys
                515                 520                 525
Ser Val Lys Ser Arg Glu Gln Leu Ser Glu Tyr Leu Thr Val Val Ile
        530                 535                 540
Phe Thr Ala Ser Ala Gln His Ala Ala Val Asn Phe Gly Gln Tyr Asp
545                 550                 555                 560
Trp Cys Ser Trp Ile Pro Asn Ala Pro Pro Thr Met Arg Ala Pro Pro
                565                 570                 575
Pro Thr Ala Lys Gly Val Val Thr Ile Glu Gln Ile Val Asp Thr Leu
                580                 585                 590
Pro Asp Arg Gly Arg Ser Cys Trp His Leu Gly Ala Val Trp Ala Leu
                595                 600                 605
Ser Gln Phe Gln Glu Asn Glu Leu Phe Leu Gly Met Tyr Pro Glu Glu
        610                 615                 620
His Phe Ile Glu Lys Pro Val Lys Glu Ala Met Ala Arg Phe Arg Lys
625                 630                 635                 640
Asn Leu Glu Ala Ile Val Ser Val Ile Ala Glu Arg Asn Lys Lys Lys
                645                 650                 655
Gln Leu Pro Tyr Tyr Tyr Leu Ser Pro Asp Arg Ile Pro Asn Ser Val
                660                 665                 670
Ala Ile
```

<210> SEQ ID NO 3
<211> LENGTH: 873

<212> TYPE: DNA
<213> ORGANISM: Homo sapiens

<400> SEQUENCE: 3

```
acttcccctt cctgtacagg gcaggttgtg cagctggagg cagagcagtc ctctctgggg      60
agcctgaagc aaacatggat caagaaactg taggcaatgt tgtcctgttg ccatcgtca      120
ccctcatcag cgtggtccag aatggattct ttgcccataa agtggagcac gaaagcagga      180
cccagaatgg gaggagcttc cagaggaccg gaacacttgc ctttgagcgg gtctacactg      240
ccaaccagaa ctgtgtagat gcgtacccca ctttcctcgc tgtgctctgg tctgcggggc      300
tactttgcag ccaagttcct gctgcgtttg ctggactgat gtacttgttt gtgaggcaaa      360
agtactttgt cggttaccta ggagagagaa cgcagagcac ccctggctac atatttggga      420
aacgcatcat actcttcctg ttcctcatgt ccgttgctgg catattcaac tattacctca      480
tcttcttttt cggaagtgac tttgaaaact acataaagac gatctccacc accatctccc      540
ctctacttct cattccctaa ctctctgctg aatatggggt tggtgttctc atctaatcaa      600
tacctacaag tcatcataat tcagctcttg agagcattct gctcttcttt agatggctgt      660
aaatctattg gccatctggg cttcacagct tgagttaacc ttgcttttcc gggaacaaaa      720
tgatgtcatg tcagctccgc cccttgaaca tgaccgtggc cccaaatttg ctattcccat      780
gcattttgtt tgtttcttca cttatcctgt tctctgaaga tgttttgtga ccaggtttgt      840
gttttcttaa aataaaatgc agagacatgt ttt                                    873
```

<210> SEQ ID NO 4
<211> LENGTH: 161
<212> TYPE: PRT
<213> ORGANISM: Homo sapiens

<400> SEQUENCE: 4

```
Met Asp Gln Glu Thr Val Gly Asn Val Val Leu Leu Ala Ile Val Thr
  1               5                  10                  15
Leu Ile Ser Val Val Gln Asn Gly Phe Phe Ala His Lys Val Glu His
                 20                  25                  30
Glu Ser Arg Thr Gln Asn Gly Arg Ser Phe Gln Arg Thr Gly Thr Leu
             35                  40                  45
Ala Phe Glu Arg Val Tyr Thr Ala Asn Gln Asn Cys Val Asp Ala Tyr
         50                  55                  60
Pro Thr Phe Leu Ala Val Leu Trp Ser Ala Gly Leu Leu Cys Ser Gln
 65                  70                  75                  80
Val Pro Ala Ala Phe Ala Gly Leu Met Tyr Leu Phe Val Arg Gln Lys
                 85                  90                  95
Tyr Phe Val Gly Tyr Leu Gly Glu Arg Thr Gln Ser Thr Pro Gly Tyr
                100                 105                 110
Ile Phe Gly Lys Arg Ile Ile Leu Phe Leu Phe Leu Met Ser Val Ala
            115                 120                 125
Gly Ile Phe Asn Tyr Tyr Leu Ile Phe Phe Gly Ser Asp Phe Glu
        130                 135                 140
Asn Tyr Ile Lys Thr Ile Ser Thr Thr Ile Ser Pro Leu Leu Leu Ile
145                 150                 155                 160
Pro
```

<210> SEQ ID NO 5
<211> LENGTH: 4465
<212> TYPE: DNA

<213> ORGANISM: Homo sapiens

<400> SEQUENCE: 5

```
caattgtcat acgacttgca gtgagcgtca ggagcacgtc caggaactcc tcagcagcgc        60
ctccttcagc tccacagcca gacgccctca gacagcaaag cctacccccg cgccgcgccc       120
tgcccgccgc tcggatgctc gcccgcgccc tgctgctgtg cgcggtcctg gcgctcagcc       180
atacagcaaa tccttgctgt tcccacccat gtcaaaaccg aggtgtatgt atgagtgtgg       240
gatttgacca gtataagtgc gattgtaccc ggacaggatt ctatggagaa aactgctcaa       300
caccggaatt tttgacaaga ataaaattat ttctgaaacc cactccaaac acagtgcact       360
acatacttac ccacttcaag ggattttgga acgttgtgaa taacattccc ttccttcgaa       420
atgcaattat gagttatgtc ttgacatcca gatcacattt gattgacagt ccaccaactt       480
acaatgctga ctatggctac aaaagctggg aagccttctc taacctctcc tattatacta       540
gagcccttcc tcctgtgcct gatgattgcc cgactccctt gggtgtcaaa ggtaaaaagc       600
agcttcctga ttcaaatgag attgtggaaa aattgcttct aagaagaaag ttcatccctg       660
atccccaggg ctcaaacatg atgtttgcat tctttgccca gcacttcacg catcagtttt       720
tcaagacaga tcataagcga gggccagctt tcaccaacgg gctgggccat ggggtggact       780
taaatcatat ttacggtgaa actctggcta gacagcgtaa actgcgcctt tcaaggatg       840
gaaaaatgaa atatcagata attgatggag agatgtatcc tcccacagtc aaagatactc       900
aggcagagat gatctaccct cctcaagtcc ctgagcatct acggtttgct gtggggcagg       960
aggtctttgg tctggtgcct ggtctgatga tgtatgccac aatctggctg cgggaacaca      1020
acagagtatg cgatgtgctt aaacaggagc atcctgaatg gggtgatgag cagttgttcc      1080
agacaagcag gctaatactg ataggagaga ctattaagat tgtgattgaa gattatgtgc      1140
aacacttgag tggctatcac ttcaaactga aatttgaccc agaactactt ttcaacaaac      1200
aattccagta ccaaaatcgt attgctgctg aatttaacac cctctatcac tggcatcccc      1260
ttctgcctga cacctttcaa attcatgacc agaaatacaa ctatcaacag tttatctaca      1320
acaactctat attgctggaa catggaatta cccagtttgt tgaatcattc accaggcaaa      1380
ttgctggcag ggttgctggt ggtaggaatg ttccacccgc agtacagaaa gtatcacagg      1440
cttccattga ccagagcagg cagatgaaat accagtcttt taatgagtac cgcaaacgct      1500
ttatgctgaa gccctatgaa tcatttgaag aacttacagg agaaaaggaa atgtctgcag      1560
agttggaagc actctatggt gacatcgatg ctgtggagct gtatcctgcc cttctggtag      1620
aaaagcctcg gccagatgcc atctttggtg aaaccatggt agaagttgga gcaccattct      1680
ccttgaaagg acttatgggt aatgttatat gttctcctgc ctactggaag ccaagcactt      1740
ttggtggaga gtgggtttt caaatcatca acactgcctc aattcagtct ctcatctgca      1800
ataacgtgaa gggctgtccc tttacttcat tcagtgttcc agatccagag ctcattaaaa      1860
cagtcaccat caatgcaagt tcttcccgct ccggactaga tgatatcaat cccacagtac      1920
tactaaaaga acgttcgact gaactgtaga agtctaatga tcatatttat ttatttatat      1980
gaaccatgtc tattaattta attatttaat aatatttata ttaaactcct tatgttactt      2040
aacatcttct gtaacagaag tcagtactcc tgttgcggag aaaggagtca tacttgtgaa      2100
gactttatg tcactactct aaagattttg ctgttgctgt taagtttgga aaacagtttt      2160
tattctgttt tataaaccag agagaaatga gttttgacgt cttttttactt gaatttcaac      2220
ttatattata agaacgaaag taaagatgtt tgaatactta aacactatca caagatggca      2280
```

```
aaatgctgaa agttttaca ctgtcgatgt ttccaatgca tcttccatga tgcattagaa    2340
gtaactaatg tttgaaattt taaagtactt ttggttattt ttctgtcatc aaacaaaaac    2400
aggtatcagt gcattattaa atgaatattt aaattagaca ttaccagtaa tttcatgtct    2460
actttttaaa atcagcaatg aaacaataat ttgaaatttc taaattcata gggtagaatc    2520
acctgtaaaa gcttgtttga tttcttaaag ttattaaact tgtacatata ccaaaaagaa    2580
gctgtcttgg atttaaatct gtaaaatcag atgaaatttt actacaattg cttgttaaaa    2640
tattttataa gtgatgttcc ttttcacca agagtataaa cctttttagt gtgactgtta    2700
aaacttcctt ttaaatcaaa atgccaaatt tattaaggtg gtggagccac tgcagtgtta    2760
tctcaaaata agaatatttt gttgagatat tccagaattt gtttatatgg ctggtaacat    2820
gtaaaatcta tatcagcaaa agggtctacc tttaaaataa gcaataacaa agaagaaaac    2880
caaattattg ttcaaattta ggtttaaaact tttgaagcaa acttttttt atccttgtgc    2940 actgcaggcc tggtactcag attttgctat gaggttaatg aagtaccaag ctgtgcttga    3000
ataacgatat gttttctcag attttctgtt gtacagttta atttagcagt ccatatcaca    3060
ttgcaaaagt agcaatgacc tcataaaata cctcttcaaa atgcttaaat tcatttcaca    3120
cattaatttt atctcagtct tgaagccaat tcagtaggtg cattggaatc aagcctggct    3180
acctgcatgc tgttccttt ctttcttct tttagccatt ttgctaagag acacagtctt    3240
ctcatcactt cgtttctcct attttgtttt actagttta agatcagagt tcactttctt    3300
tggactctgc ctatattttc ttacctgaac ttttgcaagt tttcaggtaa acctcagctc    3360
aggactgcta tttagctcct cttaagaaga ttaaaagaga aaaaaaaagg cccttttaaa    3420
aatagtatac acttatttta agtgaaaagc agagaatttt atttatagct aattttagct    3480
atctgtaacc aagatggatg caaagaggct agtgcctcag agagaactgt acggggtttg    3540
tgactggaaa aagttacgtt cccattctaa ttaatgccct ttcttattta aaacaaaac    3600 caaatgatat ctaagtagtt ctcagcaata ataatga cgataatact tcttttccac    3660
atctcattgt cactgacatt taatggtact gtatattact taatttattg aagattatta    3720
tttatgtctt attaggacac tatggttata aactgtgttt aagcctacaa tcattgattt    3780
ttttttgtta tgtcacaatc agtatatttt ctttggggtt acctctctga atattatgta    3840
aacaatccaa agaaatgatt gtattaagat ttgtgaataa atttttagaa atctgattgg    3900
catattgaga tatttaaggt tgaatgtttg tccttaggat aggcctatgt gctagcccac    3960
aaagaatatt gtctcattag cctgaatgtg ccataagact gacctttaa aatgttttga    4020 gggatctgtg gatgcttcgt taatttgttc agccacaatt tattgagaaa atattctgtg    4080
tcaagcactg tgggttttaa tattttaaaa tcaaacgctg attacagata atagtattta    4140
tataaataat tgaaaaaaat tttcttttgg gaagagggag aaaatgaaat aaatatcatt    4200
aaagataact caggagaatc ttctttacaa ttttacgttt agaatgttta aggttaagaa    4260
agaaatagtc aatatgcttg tataaaacac tgttcactgt ttttttaaa aaaaaaactt    4320 gatttgttat taacattgat ctgctgacaa aacctgggaa tttgggttgt gtatgcgaat    4380
gtttcagtgc ctcagacaaa tgtgtattta acttatgtaa aagataagtc tggaaataaa    4440
tgtctgttta ttttgtact attta                                          4465
```

<210> SEQ ID NO 6  
<211> LENGTH: 604  
<212> TYPE: PRT

<213> ORGANISM: Homo sapiens

<400> SEQUENCE: 6

```
Met Leu Ala Arg Ala Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
                100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
            195                 200                 205

Gly Leu Gly His Gly Val Asp Leu Asn His Ile Tyr Gly Glu Thr Leu
210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile His
370                 375                 380

Asp Gln Lys Tyr Asn Tyr Gln Gln Phe Ile Tyr Asn Asn Ser Ile Leu
385                 390                 395                 400
```

```
                    -continued

Leu Glu His Gly Ile Thr Gln Phe Val Glu Ser Phe Thr Arg Gln Ile
                405                 410                 415

Ala Gly Arg Val Ala Gly Arg Asn Val Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 7
<211> LENGTH: 5093
<212> TYPE: DNA
<213> ORGANISM: Homo sapiens

<400> SEQUENCE: 7
aggtgacagc tggagggagg agcggggtg  gagccggggg aagggtgggg aggggatggg     60
ctggagctcc gggcagtgtg cgaggcgcac gcacaggagc ctgcactctg cgtcccgcac    120
cccagcagcc gcgccatgag ccggagtctc ttgctctggt tcttgctgtt cctgctcctg    180
ctcccgccgc tcccgtcct  gctcgcggac ccaggggcgc ccacgccagt gaatccctgt    240
tgttactatc catgccagca ccagggcatc tgtgtccgct tcggccttga ccgctaccag    300
tgtgactgca cccgcacggg ctattccggc cccaactgca ccatccctgg cctgtggacc    360
tggctccgga attcactgcg gcccagcccc tctttcaccc acttcctgct cactcacggg    420
cgctggttct gggagtttgt caatgccacc ttcatccgag atgctcat  gcgcctggta    480 ctcacagtgc gctccaacct tatcccagt  ccccccacct acaactcagc acatgactac    540
atcagctggg agtctttctc caacgtgagc tattacactc gtattctgcc ctctgtgcct    600
aaagattgcc ccacacccat gggaaccaaa gggaagaagc agttgccaga tgcccagctc    660
ctggcccgcc gcttcctgct caggaggaag ttcatacctg accccaagg  caccaacctc    720 atgtttgcct tctttgcaca acacttcacc caccagttct tcaaaacttc tggcaagatg    780
ggtcctggct tcaccaaggc cttgggccat ggggtagacc tcggccacat ttatggagac    840
aatctggagc gtcagtatca actgcggctc tttaaggatg ggaaactcaa gtaccaggtg    900
ctggatggag aaatgtaccc gcccctcgta gaagaggcgc ctgtgttgat gcactacccc    960
```

```
cgaggcatcc cgccccagag ccagatggct gtgggccagg aggtgtttgg gctgcttcct   1020
gggctcatgc tgtatgccac gctctggcta cgtgagcaca accgtgtgtg tgacctgctg   1080
aaggctgagc accccacctg gggcgatgag cagcttttcc agacgacccg cctcatcctc   1140
atagggagac catcaagat tgtcatcgag gagtacgtgc agcagctgag tggctatttc    1200
ctgcagctga aatttgaccc agagctgctg ttcggtgtcc agttccaata ccgcaaccgc   1260
attgccatgg agttcaacca tctctaccac tggcaccccc tcatgcctga ctccttcaag   1320
gtgggctccc aggagtacag ctacgagcag ttcttgttca cacctccat gttggtggac    1380 tatggggttg aggccctggt ggatgccttc tctcgccaga ttgctggccg gatcggtggg   1440
ggcaggaaca tggaccacca catcctgcat gtggctgtgg atgtcatcag ggagtctcgg   1500
gagatgcggc tgcagccctt caatgagtac cgcaagaggt ttggcatgaa acctacacc    1560 tccttccagg agctcgtagg agagaaggag atggcagcag agttggagga attgtatgga   1620
gacattgatg cgttggagtt ctaccctgga ctgcttcttg aaaagtgcca tccaaactct   1680
atctttgggg agagtatgat agagattggg gctccctttt ccctcaaggg tctcctaggg   1740
aatcccatct gttctccgga gtactggaag ccgagcacat ttggcggcga ggtgggcttt   1800
aacattgtca agacggccac actgaagaag ctggtctgcc tcaacaccaa gacctgtccc   1860
tacgtttcct tccgtgtgcc ggatgccagt caggatgatg gcctgctgt ggagcgacca    1920 tccacagagc tctgaggggc aggaaagcag cattctggag gggagagctt tgtgcttgtc   1980
attccagagt gctgaggcca gggctgatgg tcttaaatgc tcattttctg gtttggcatg   2040
gtgagtgttg gggttgacat ttagaacttt aagtctcacc cattatctgg aatattgtga   2100
ttctgtttat tcttccagaa tgctgaactc cttgttagcc cttcagattg ttaggagtgg   2160
ttctcatttg gtctgccaga atactgggtt cttagttgac aacctagaat gtcagatttc   2220
tggttgattt gtaacacagt cattctagga tgtggagcta ctgatgaaat ctgctagaaa   2280 gttaggggt tcttatttg cattccagaa tcttgacttt ctgattggtg attcaaagtg     2340
ttgtgttcct ggctgatgat ccagaacagt ggctcgtatc ccaaatctgt cagcatctgg   2400
ctgtctagaa tgtggatttg attcattttc ctgttcagtg agatatcata gagacggaga   2460
tcctaaggtc caacaagaat gcattccctg aatctgtgcc tgcactgaga gggcaaggaa   2520
gtggggtgtt cttcttggga cccccactaa gaccctggtc tgaggatgta gagagaacag   2580
gtgggctgta ttcacgccat tggttggaag ctaccagagc tctatcccca tccaggtctt   2640
gactcatggc agctgtttct catgaagcta ataaaattcg ctttctaaag ttacctgtta   2700
tatatctctt ttggtcccat cctctaaagc agaggcaaca ctggaacatg gctagccttt   2760
cttgtagcca tggctgggcg tgctagaggt tgcagcatga gactttctgc tgggatcctt   2820
gggcccatca ctgtatagac atgctaccac tggtacttcc tttctccctg cgggccaggc   2880
actgcccttt tcaggaagct ctcttaaaat acccattgcc ccagacctgg aagatataac   2940
attcagttcc caccatctga ttaaaacaac ttcctccctt acagagcata acacagaggg   3000
ggcacccggg gaggagagca catactgtgt tccaatttca cgcttttaat tctcatttgt   3060
tctcacacca acagtgtgaa gtgcgtggta taatctccat ttcaaaacca aggaagcagc   3120
ctcagagtgg tcgagtgaca cacctcacgc aggctgagtc cagagcttgt gctcctcttg   3180
attcctggtt tgactcagtt ccaggcctga tcttgcctgt ctggctcagg gtcaaagaca   3240
gaatggtgga gtgtagcctc cacctgatat tcaggctact cattcagtcc caaatatgta   3300
ttttcctaag tgtttactat gtgccagttc ctgtaacagg tgtggggaca cagcagtgag   3360
```

```
taatcaatac agacaaggtt ctgcccttat ggagctcaca ctccagtggc agacaaacag    3420
accataaata aggaaacgat gaaataagat atatacaagg tgagtgtgac ttcccttcta    3480
accccctctg ctctgtcctc ccctattgcg ctctcaagac cagagaccca acagcagtga    3540
tctcagggca gacagccctc cactccagct ctgagaccct tttctcagga cctctgtagg    3600
cagcagagag agaggacaga gggtaagat gaggggttga gggaaggttc ttcatgatcc    3660
acactttggg cttagtattt ctcaggaaga gctatggccc agaaacaaca ggggaaacta    3720
gagttcggtc tgacagtcct tggggttaag tctcctgtct tatggtccag aaactcctgt    3780
ttctccttag ttggctggaa actgctccca tcattccttc tggcctctgc tgaatgcagg    3840
gaatgcaatc cttccctgct cttgcagttg ctctgacgta gaaagatcct tcgggtgctg    3900
gaagtctcca tgaagagctt gtgtcctgtc cttcttgca gattctattt ccctcttct    3960 gctaatacct cttactttgc ttgagaatcc tctcctttct tattaatttc agtcttggtg    4020
gttctatcag gggtgcattc tggccaaggg gtgggcctgt gaatcaatcc tgggcaatca    4080
gacaccctct ccttaaaaac tggcccgtgg agactgagat cactgactct gactcatccc    4140
cacagctggc tctgacaaga tggtccattt gttcctgctt ccgagatccc cagggcagcc    4200
tggatccctg cccttctcaa gactttagct tttccttcca tccggtggcc tattccagga    4260
attcctcttt tgcttaaatc agttggagtt tgtgtctgtt gcttgtaatc aagcctttat    4320
ggctgctggg ctgagtgaca caagcacttt aatggcctgg agggacttttt aatcagtgaa    4380 gatgcaatca gacaagtgtt ttggaaagag caccctcgag aagggtggat gacagggcag    4440
agcaggaagg acaggaagct ggcagaacgg aggaggctgc agccgtggtc caaccaggag    4500
ctgatggcag ctgggctag ggaagggct ttgagggtgg aaggatggga tgggttccag    4560
aggtattcct ctcttaaatg caagtgccta gattaggtag actttgctta gtattgacaa    4620
ctgcacatga aagttttgca aagggaaaca ggctaaatgc accaagaaag cttcttcaga    4680
gtgaagaatc ttaatgcttg taatttaaac atttgttcct ggagttttga tttggtggat    4740
gtgatggttg gttttatttg tcagtttggt tgggctatag cacacagtta tttaatcaaa    4800
cagtaatcta ggtgtggctg tgaaggtatt ttgtagatgt gattaacatc tacaatcagt    4860
tgactttaag tgaaagagat tacttaaata atttgggtga gctgcacctg attagttgaa    4920
aggcctcaag aacaaacact gcagtttcct ggaaaagaag aaactttgcc tcaagactat    4980
agccatcgac tcctgcctga gtttccagcc tgctagtctg ccctatggat ttgaagtttg    5040
ccaaccccaa caattgtgtg aattaatttc taaaaataaa gctatataca gcc           5093
```

<210> SEQ ID NO 8
<211> LENGTH: 599
<212> TYPE: PRT
<213> ORGANISM: Homo sapiens

<400> SEQUENCE: 8

```
Met Ser Arg Ser Leu Leu Leu Trp Phe Leu Leu Phe Leu Leu Leu Leu
1               5                   10                  15

Pro Pro Leu Pro Val Leu Leu Ala Asp Pro Gly Ala Pro Thr Pro Val
                20                  25                  30

Asn Pro Cys Cys Tyr Tyr Pro Cys Gln His Gln Gly Ile Cys Val Arg
            35                  40                  45

Phe Gly Leu Asp Arg Tyr Gln Cys Asp Cys Thr Arg Thr Gly Tyr Ser
        50                  55                  60
```

```
Gly Pro Asn Cys Thr Ile Pro Gly Leu Trp Thr Trp Leu Arg Asn Ser
 65                  70                  75                  80

Leu Arg Pro Ser Pro Ser Phe Thr His Phe Leu Thr His Gly Arg
             85                  90                  95

Trp Phe Trp Glu Phe Val Asn Ala Thr Phe Ile Arg Glu Met Leu Met
            100                 105                 110

Arg Leu Val Leu Thr Val Arg Ser Asn Leu Ile Pro Ser Pro Pro Thr
            115                 120                 125

Tyr Asn Ser Ala His Asp Tyr Ile Ser Trp Glu Ser Phe Ser Asn Val
            130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Ala Gln His Phe Thr His Gln Phe
            195                 200                 205

Phe Lys Thr Ser Gly Lys Met Gly Pro Gly Phe Thr Lys Ala Leu Gly
210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
                245                 250                 255

Asp Gly Glu Met Tyr Pro Pro Ser Val Glu Ala Pro Val Leu Met
                260                 265                 270

His Tyr Pro Arg Gly Ile Pro Pro Gln Ser Gln Met Ala Val Gly Gln
            275                 280                 285

Glu Val Phe Gly Leu Leu Pro Gly Leu Met Leu Tyr Ala Thr Leu Trp
290                 295                 300

Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
                325                 330                 335

Gly Glu Thr Ile Lys Ile Val Ile Glu Glu Tyr Val Gln Gln Leu Ser
            340                 345                 350

Gly Tyr Phe Leu Gln Leu Lys Phe Asp Pro Glu Leu Leu Phe Gly Val
            355                 360                 365

Gln Phe Gln Tyr Arg Asn Arg Ile Ala Met Glu Phe Asn His Leu Tyr
            370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
                405                 410                 415

Gly Val Glu Ala Leu Val Asp Ala Phe Ser Arg Gln Ile Ala Gly Arg
            420                 425                 430

Ile Gly Gly Gly Arg Asn Met Asp His His Ile Leu His Val Ala Val
            435                 440                 445

Asp Val Ile Arg Glu Ser Arg Glu Met Arg Leu Gln Pro Phe Asn Glu
450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Glu Leu Tyr Gly Asp
```

-continued

```
                    485                 490                 495
Ile Asp Ala Leu Glu Phe Tyr Pro Gly Leu Leu Leu Glu Lys Cys His
                500                 505                 510

Pro Asn Ser Ile Phe Gly Glu Ser Met Ile Glu Ile Gly Ala Pro Phe
            515                 520                 525

Ser Leu Lys Gly Leu Leu Gly Asn Pro Ile Cys Ser Pro Glu Tyr Trp
        530                 535                 540

Lys Pro Ser Thr Phe Gly Glu Val Gly Phe Asn Ile Val Lys Thr
545                 550                 555                 560

Ala Thr Leu Lys Lys Leu Val Cys Leu Asn Thr Lys Thr Cys Pro Tyr
                565                 570                 575

Val Ser Phe Arg Val Pro Asp Ala Ser Gln Asp Asp Gly Pro Ala Val
            580                 585                 590

Glu Arg Pro Ser Thr Glu Leu
        595
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aactgggcga gatccagctg g                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aagctcccgg tgaccacgga g                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaggaagcca tggcccgatt c                                            21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aatcgagaag cgcaagtact g                                            21

<210> SEQ ID NO 13
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 13
aaggagtgga ctttgttctg a                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aacttcggcc agtacgactg g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagttggccc gagatgacca a                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aacacatctg gtgtctgagg t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaccatgcga gccccgccac c                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aagcaaacat ggatcaagaa a                                              21

<210> SEQ ID NO 19
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 19
aagttcctgc tgcgtttgct g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aattcagctc ttgagagcat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatggattct ttgcccataa a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagtactttg tcggttacct a                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aatctattgg ccatctgggc t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaccagaact gtgtagatgc g                                              21

<210> SEQ ID NO 25
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 25 aagtgactttgaaaactacat                                                21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aatgatgtca tgtcagctcc g                                               21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcaggtgctt ctcgctgcag cc                                              22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gccagtactt gcgcttctcg                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccatcgatat tgtttttgcc                                                 20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggagcttctc gggcagctct gtgc                                            24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 31
ccaggttctt atacagcaag c                                      21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccagcagctt gaaaatgggg tgc                                    23

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gccccgggcc ttgatggcc                                         19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccacgccctt ggcagtcgg                                         19

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcggaatcgg gccatggctt cc                                     22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gttccggtcc tctggaagct cc                                     22

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgcagaccag agcacagcg                                           19

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcaaacgcag caggaac                                             17

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgtttcccaa atatgtagcc                                          20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gttttcaaag tcacttccg                                           19

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggttaactca agctgtgaag c                                        21

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggagctgaca tgacatc                                             17

<210> SEQ ID NO 43
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 43
ggccacggtc atgttcaagg                                                20
```